US011444251B2

(12) United States Patent
Oikawa et al.

(10) Patent No.: US 11,444,251 B2
(45) Date of Patent: Sep. 13, 2022

(54) ORGANIC ELECTROLUMINESCENT ELEMENT

(71) Applicant: KONICA MINOLTA, INC., Tokyo (JP)

(72) Inventors: Kazuhiro Oikawa, Hachioji (JP); Akihiro Kimura, Hino (JP)

(73) Assignee: MERCK PATENT GMBH, Darmstadt (DE)

( * ) Notice: Subject to any disclaimer, the term of this patent is extended or adjusted under 35 U.S.C. 154(b) by 614 days.

(21) Appl. No.: 16/349,056

(22) PCT Filed: Oct. 17, 2017

(86) PCT No.: PCT/JP2017/037607
§ 371 (c)(1),
(2) Date: May 10, 2019

(87) PCT Pub. No.: WO2018/100907
PCT Pub. Date: Jun. 7, 2018

(65) Prior Publication Data
US 2019/0288219 A1 Sep. 19, 2019

(30) Foreign Application Priority Data
Nov. 29, 2016 (JP) .............................. JP2016-231746

(51) Int. Cl.
H01L 51/00 (2006.01)
C07D 213/22 (2006.01)
C07D 271/107 (2006.01)
C07D 401/14 (2006.01)
C07D 405/14 (2006.01)
C07D 471/04 (2006.01)
C07D 471/14 (2006.01)
C07D 487/04 (2006.01)
C07D 495/04 (2006.01)
C07F 9/6568 (2006.01)
C07F 9/6571 (2006.01)
H01L 51/50 (2006.01)

(52) U.S. Cl.
CPC ........ H01L 51/0072 (2013.01); C07D 213/22 (2013.01); C07D 271/107 (2013.01); C07D 401/14 (2013.01); C07D 405/14 (2013.01); C07D 471/04 (2013.01); C07D 471/14 (2013.01); C07D 487/04 (2013.01); C07D 495/04 (2013.01); C07F 9/65685 (2013.01); C07F 9/657163 (2013.01); H01L 51/007 (2013.01); H01L 51/0052 (2013.01); H01L 51/0067 (2013.01); H01L 51/0071 (2013.01); H01L 51/0073 (2013.01); H01L 51/0074 (2013.01); H01L 51/5012 (2013.01); H01L 51/5016 (2013.01); H01L 51/5072 (2013.01); H01L 2251/558 (2013.01)

(58) Field of Classification Search
CPC .............. C07D 271/107; C07D 401/14; C07D 405/14; C07D 471/04; C07D 471/14; C07D 487/04; C07D 495/04; C07F 9/65685; C07F 9/657163; H01L 2251/558; H01L 51/0037; H01L 51/0052; H01L 51/0061; H01L 51/0067; H01L 51/007; H01L 51/0071; H01L 51/0072; H01L 51/0073; H01L 51/0074; H01L 51/0081; H01L 51/0085; H01L 51/5004; H01L 51/5012; H01L 51/5016; H01L 51/5072
See application file for complete search history.

(56) References Cited

U.S. PATENT DOCUMENTS

| 2013/0119360 | A1* | 5/2013 | Katakura | ............ | C07D 405/04 257/40 |
| 2013/0200340 | A1* | 8/2013 | Otsu | .................. | C07F 15/0033 257/40 |
| 2016/0285008 | A1* | 9/2016 | Okubo | ................ | C08G 61/122 |

FOREIGN PATENT DOCUMENTS

| CN | 103548172 | A | 1/2014 |
| JP | 2003-007467 | A | 1/2003 |
| JP | 2003288988 | A | 10/2003 |
| JP | 2004-265672 | A | 9/2004 |
| JP | 4626515 | B2 | 2/2011 |
| JP | 4915651 | B2 | 4/2012 |
| JP | 2014519189 | A | 8/2014 |
| JP | 2015037168 | A | 2/2015 |
| JP | 5933691 | B2 | 6/2016 |
| WO | 2008035595 | A1 | 3/2008 |
| WO | 20090063850 | A1 | 5/2009 |

OTHER PUBLICATIONS

Machine translation of JP 2003-288988 (publication date Oct. 2003). (Year: 2003).*
CNIPA, Office Action for the corresponding Chinese patent application No. 201780072141.6, dated Sep. 29, 2020, with English translation.
International Search Report and Written Opinion dated Jan. 23, 2018 for International Application No. PCT/JP2017/037607 and English translation.

(Continued)

Primary Examiner — Dawn L Garrett
(74) Attorney, Agent, or Firm — Lucas & Mercanti, LLP

(57) ABSTRACT

Provided is an organic electroluminescent element having high efficiency, a long lifetime, and bending resistance. An organic electroluminescent element includes a light emitting layer and an electron transport layer adjacent to the light emitting layer between a positive electrode and a negative electrode. A host compound of the light emitting layer has an ionization potential deeper than that of a light emitting dopant of the light emitting layer by 0.3 eV or more. At least one organic compound contained in the electron transport layer has a molecular dipole moment of 6.0 debye or more.

15 Claims, 1 Drawing Sheet

(56) References Cited

OTHER PUBLICATIONS

JPO, Office Action for the corresponding Japanese patent application No. 2018-553703, dated Aug. 31, 2021, with English translation.

* cited by examiner

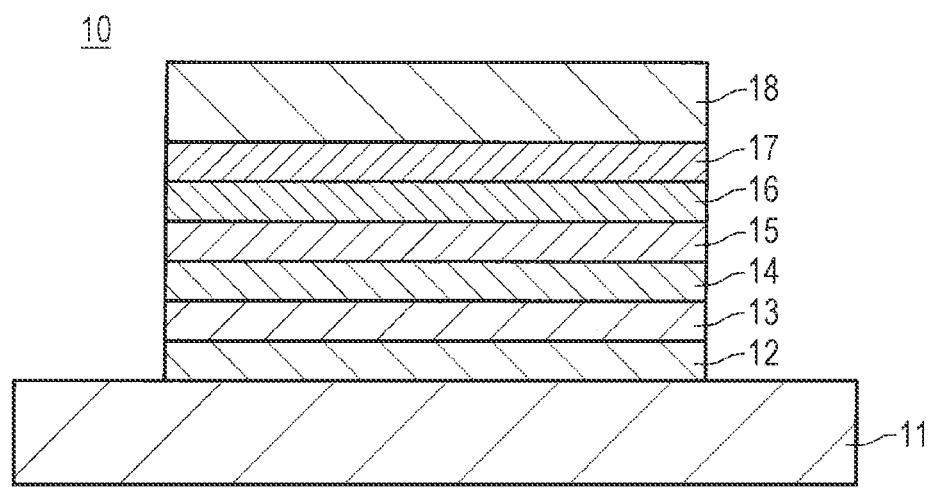

ORGANIC ELECTROLUMINESCENT ELEMENT

CROSS REFERENCE TO RELATED APPLICATION

This Application is a 371 of PCT/JP2017/037607 filed on Oct. 17, 2017 which, in turn, claimed the priority of Japanese Patent Application No. 2016-231746 filed on Nov. 29, 2016, both applications are incorporated herein by reference.

TECHNICAL FIELD

The present invention relates to an organic electroluminescent element.

BACKGROUND ART

As attractiveness of an organic electroluminescent element (hereinafter appropriately referred to as an organic EL element) as a surface light emitting body and a high efficiency light source increases, an organic EL element satisfying all of high efficiency, a long lifetime, and low cost has been required.

Furthermore, in order to maximize attractiveness of a light source, such as thinness, lightness, or bending, development of a flexible display and flexible lighting with an organic EL element formed on a flexible panel has been advanced. In order to realize the flexible display and the flexible lighting, high manufacturing technology and material technology are required. In particular, a flexible panel that does not lower luminance, does not generate a dark spot, and does not cause unevenness in luminance against bending has been required.

In response to these demands, performance has been enhanced by a method for forming a multilayer structure by a vapor deposition method using functional materials. However, manufacturing cost is high disadvantageously due to manufacturing facilities for realizing a high degree of vacuum and low utilization efficiency of materials. Meanwhile, as a method for lowering manufacturing cost, there is a method for laminating functional materials by a wet method (also referred to as a coating method).

However, many functional materials constituting the layers are formed by structural skeletons chemically similar to each other. This means that the functional materials have close solubility in a solvent for lamination by coating, and are mixed at the time of lamination. Even in a case where lamination is attempted by using a difference in solubility between a solvent and a solute, an upper limit of the lamination number is three or four. Therefore, in a case of the wet method, it is difficult to adopt a function separation multilayer structure as in the vapor deposition method. In a method for laminating functional materials by the wet method, in order to achieve both high efficiency by low voltage and a long lifetime, there is a very high technical hurdle.

In order to achieve both high efficiency and a long lifetime, a technology of using a polar compound for an electron transport material is disclosed (for example, see Patent Literatures 1 to 4).

Patent Literature 1 discloses a multi-membered ring compound containing a hetero nitrogen atom as a polar hole blocking material. However, in the compound, a film density or electron transportability in a film in a case where a solvent is used for film formation is not taken into consideration, and an organic EL element using the compound has room for improvement in performance.

Patent Literature 2 realizes high polarity by subjecting a phosphine oxide-based electron transport material and an alkali metal complex to co-vapor deposition. However, the alkali metal complex generates a quencher, and therefore performance of an organic light emitting element is deteriorated disadvantageously. In a case where a film is formed by coating, dissociation of a complex is not sufficient, and an effect of using the phosphine oxide-based electron transport material and the alkali metal complex cannot be obtained.

Patent Literature 3 mixes a material having a dipole moment of 2 debye or more with a material constituting an electron transport layer. However, as the material having a dipole moment of 2 debye or more, the same compound as a light emitting dopant is used, and not a little interfacial light emission with the electron transport material is present. Therefore, this is not sufficient for obtaining high performance in an organic EL element. In a case where the same component as the component of the light emitting layer is applied to form an electron transport layer, a lower layer is washed away by a soluble solvent. Therefore, a sufficient effect cannot be obtained with a coating type organic EL element disadvantageously.

Patent Literature 4 uses a high-polarity electron transport material as a host material to lower voltage. However, if the polarity is too strong, a recombination probability decreases, and light emission efficiency decreases due to interaction with a light emitting material. Therefore, performance of an organic EL element is not sufficient. In addition, an electron moves too fast, and the light emitting material and the electron transport material coexist disadvantageously.

Furthermore, none of the Patent Literatures mentions bending durability in a case where an element is manufactured on a flexible substrate. An organic EL element using these polar compounds has room for improvement in bending durability.

CITATION LIST

Patent Literature

Patent Literature 1: JP 4626515 B2
Patent Literature 2: JP 5933691 B2
Patent Literature 3: JP 4915651 B2
Patent Literature 4: JP 2015-037168 A

SUMMARY OF INVENTION

Technical Problem

An object of the present invention is to provide an organic electroluminescent element having high efficiency, a long lifetime, and bending resistance.

Solution to Problem

In order to solve the above problems, the present inventor has found the following matters in a process of examining a cause and the like of the above problems.

A material capable of obtaining blue phosphorescence with high efficiency and a long lifetime is a low molecular substance from a viewpoint of achieving high S1 and high Ti and a viewpoint of quenching due to impurities and an unreacted group. In order to achieve high performance thereof, a charge blocking function and an exciton blocking function of a light emitting layer are required for a layer adjacent to the light emitting layer. Furthermore, due to an interfacial electric field generated by using a material having a large dipole moment for the light emitting layer and the electron transport layer, it is possible to mitigate an injection barrier to lower voltage.

In the present invention, it is possible to achieve low voltage and a long lifetime with an electron transport material having a dipole moment of 6.0 debye or more.

However, when a low molecular light emitting material directly comes into contact with an electron transport material containing a large number of hetero atoms and having large basicity (nucleophilicity), a quencher of light emission is generated by ligand exchange, complex formation, or the like, resulting in a decrease in light emission efficiency disadvantageously.

In the present invention, it has been found that both high efficiency and a long lifetime can be achieved by using a host compound having an ionization potential (hereinafter appropriately referred to as Ip) deeper than a light emitting material (Δ0.3 eV or more) in a light emitting layer. It is considered that this is because Ip of a dopant acts as a hole trap, recombination occurs on a side of a hole transport layer, and therefore an influence of the electron transport material is small.

Furthermore, within a π conjugation of an electron transport material molecule, a distance between N (nitrogen) atoms is short, and a dipole is large to improve intramolecular transportability. In addition, solubility in various solvents is high due to a high N density, and an amorphous property can be maintained, whereas an interaction between adjacent molecules is large, a density is increased at the time of film formation, a solvent which is a factor for deteriorating performance is easily expelled, and molecular orientation is in parallel to a substrate. Therefore, external extraction efficiency is improved. In addition, a film having a high density due to a high N density is resistant to film quality change due to heat generated by element driving. Furthermore, the film having a high density due to a high N density suppresses arrival of oxygen, water, or the like entering an element at a light emitting layer. Therefore, it has been found that a decrease in luminance during storage at high temperature is suppressed, and an increase in voltage can be suppressed in a case where an organic layer is cracked by bending.

The effect of the present invention is easily exhibited in a case where both the light emitting layer and the electron transport layer are formed by coating. In a case where a film is formed by coating, interfacial mixing is more significant and a light emitting material is more easily affected by an electron transport material than in a case where a film is formed by vapor deposition. However, even in such a case, high efficiency, a long lifetime, and bending durability can be achieved, and it is unnecessary to insert a block layer or the like. Therefore, manufacturing cost can be reduced. The present invention is particularly suitable for a case where manufacture is performed by film formation using coating in which the number of lamination cannot be increased.

The above problems according to the present invention can be solved by the following means.

1. An organic electroluminescent element including: a light emitting layer; and an electron transport layer adjacent to the light emitting layer between a positive electrode and a negative electrode, in which a host compound of the light emitting layer has an ionization potential deeper than that of a light emitting dopant of the light emitting layer by 0.3 eV or more, and at least one organic compound contained in the electron transport layer has a molecular dipole moment of 6.0 debye or more.

2. The organic electroluminescent element according to the item 1, in which the molecular dipole moment of the organic compound is 8.0 debye or more.

3. The organic electroluminescent element according to the item 1, in which the molecular dipole moment of the organic compound is 10.0 debye or more.

4. The organic electroluminescent element according to the item 1, in which the molecular dipole moment of the organic compound is 12.0 debye or more.

5. The organic electroluminescent element according to any one of the items 1 to 4, in which the organic compound is a compound represented by the following general formula (1).

[Chemical formula 1]

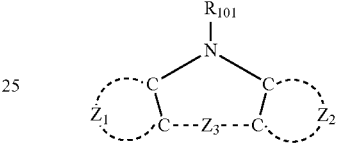

General formula (1)

[In the formula, $Z_1$ and $Z_2$ each independently represent a 6-membered aromatic hydrocarbon ring or a 6-membered aromatic heterocyclic ring which may have a substituent, and $Z_3$ represents a simple bond. $R_{101}$ represents an aryl group which may have a substituent or an aromatic heterocyclic group which may have a substituent.]

6. The organic electroluminescent element according to the item 5, in which in the general formula (1), $Z_1$ represents a pyridine ring which may have a substituent, and $Z_2$ represents a benzene ring which may have a substituent.

7. The organic electroluminescent element according to the item 5, in which in the general formula (1), $Z_1$ and $Z_2$ each represent a pyridine ring which may have a substituent.

8. The organic electroluminescent element according to any one of the items 5 to 7, in which the organic compound is a compound represented by general formula (1), containing only carbon, nitrogen, and hydrogen.

9. The organic electroluminescent element according to any one of the items 1 to 8, in which a whole of constituent layers of the organic electroluminescent element contains a polar fluorinated solvent in an amount of 1000 ppm by mass or less.

10. The organic electroluminescent element according to the item 9, in which the polar fluorinated solvent is any one or more selected from a fluorinated alcohol, a fluorinated ester, and a fluorinated ether.

11. The organic electroluminescent element according to the item 9 or 10, in which the polar fluorinated solvent contains a fluorinated alcohol having 3 to 5 carbon atoms.

12. The organic electroluminescent element according to any one of the items 1 to 11, in which the light emitting layer is formed of a compound having a molecular weight of 3,000 or less.

13. The organic electroluminescent element according to any one of the items 1 to 12, in which the light emitting layer has a film thickness of 50 nm or more.

Advantageous Effects of Invention

The present invention can provide an organic electroluminescent element having high efficiency, a long lifetime, and bending resistance.

BRIEF DESCRIPTION OF DRAWINGS

The FIGURE is a schematic cross-sectional view of an organic EL element.

DESCRIPTION OF EMBODIMENTS

Hereinafter, embodiments for performing the present invention will be described in detail, but the present invention is not limited thereto. Incidentally, in the present application, "to" means inclusion of numerical values described before and after "to" as a lower limit value and an upper limit value.

<<Organic Electroluminescent Element>>

An organic EL element includes a light emitting layer and an electron transport layer adjacent to the light emitting layer between a positive electrode and a negative electrode.

In the organic EL element, a host compound of the light emitting layer has an ionization potential (Ip) deeper than that of a light emitting dopant of the light emitting layer by 0.3 eV or more. Furthermore, in the organic EL element, at least one organic compound contained in the electron transport layer has a molecular dipole moment of 6.0 debye or more.

The ionization potential is defined as energy required for releasing an electron of a compound at a HOMO (highest occupied molecular orbital) level to a vacuum level. The dipole moment is defined as a product of a vector of a bias of an electron density determined from density functional calculation of the compound from a negative charge to a positive charge and a magnitude thereof. The ionization potential and the dipole moment can be determined by the following method, for example.

(1) The ionization potential and the dipole moment can be determined by performing structural optimization using Gaussian 98 (Gaussian 98, Revision A. 11.4, M. J. Frisch, et al, Gaussian, Inc., Pittsburgh Pa., 2002.) which is software for calculating molecular orbital manufactured by US Gaussian, Inc. with B3LYP/6-31G® as a keyword to obtain values (a value in terms of eV unit in a case of ionization potential and a value in terms of debye unit in a case of dipole moment) and rounding off the second decimal place or the third decimal place of the calculated values. The calculated values are effective because a correlation between the calculated values determined by this method and experimental values is high.

(2) The ionization potential can also be determined by a method for directly measuring the ionization potential by photoelectron spectroscopy. For example, a low energy electron spectroscopy apparatus "Model AC-2" manufactured by Riken Keiki Co., Ltd. or a method known as ultraviolet photoelectron spectroscopy can be suitably used.

<<Configuration of Organic EL Element>>

The configuration of the organic EL element of the present invention will be described with reference to the FIGURE. The FIGURE is a schematic cross-sectional view of an organic EL element 10 which is an example of the organic EL element.

The organic EL element 10 includes a substrate 11, a positive electrode 12, a hole injection layer 13, a hole transport layer 14, a light emitting layer 15, an electron transport layer 16, an electron injection layer 17, and a negative electrode 18 in this order.

The element configuration of the organic EL element is not limited to the configuration example illustrated in the FIGURE. Examples of a layer configuration of a typical element configuration include the following configurations.

(1) light emitting layer/electron transport layer
(2) hole transport layer/light emitting layer/electron transport layer
(3) hole transport layer/light emitting layer/electron transport layer/electron injection layer
(4) hole injection layer/hole transport layer/light emitting layer//electron transport layer
(5) hole injection layer/hole transport layer/light emitting layer//electron transport layer/electron injection layer
(6) hole injection layer/hole transport layer/electron blocking layer/light emitting layer/electron transport layer/electron injection layer Among the above configurations, configurations (5) and (6) are preferably used, but the present invention is not limited thereto.

The light emitting layer is formed of a single layer or a plurality of layers. As necessary, a hole blocking layer (hole barrier layer), an electron injection layer (negative electrode buffer layer), or the like may be disposed between the light emitting layer and the negative electrode, and an electron blocking layer (electron barrier layer), a hole injection layer (positive electrode buffer layer), or the like may be disposed between the light emitting layer and the positive electrode. These layers can be formed by known materials and methods as long as satisfying the requirements of the present invention.

<<Light Emitting Layer>>

The light emitting layer provides a place where an electron and a hole injected from an electrode or an adjacent layer are recombined to emit light via an exciton. The light emitting layer contains a light emitting dopant (also referred to as a light emitting dopant compound or a dopant compound, or simply referred to as a dopant) and a host compound (also referred to as a matrix material or a light emitting host compound, or simply referred to as a host).

A light emitting layer material constituting the light emitting layer may be a compound having a molecular weight of 3,000 or less. By using a compound having a molecular weight of 3,000 or less, solubility in a solvent is improved. Note that the molecular weight is preferably 500 or more.

The molecular weight of each of the light emitting dopant and the host compound used as the light emitting layer material is not particularly limited. However, the light emitting layer according to the present invention preferably contains a compound having a dibenzofuran ring, a dibenzothiophene ring, or a carbazole ring and not having an alkyl group, an alkenyl group, an alkynyl group, or an arylalkyl group.

The film thickness of the light emitting layer is not particularly limited, but is preferably 50 nm or more, and more preferably 70 nm or more from a viewpoint of a distance between a recombination region and the electron transport layer. The film thickness is preferably 150 nm or less from a viewpoint of driving voltage.

A method for forming the light emitting layer is not particularly limited, and the light emitting layer can be formed by, for example, a conventionally known vacuum vapor deposition method or a wet method. Among these methods, the light emitting layer is preferably formed by the wet method from a viewpoint of reducing manufacturing cost of the organic EL element.

Examples of the wet method include a spin coating method, a casting method, an inkjet method, a printing method, a die coating method, a blade coating method, a roll coating method, a spray coating method, a curtain coating method, and a Langmuir-Blodgett method (LB method). Among these methods, a method applicable to a roll-to-roll method, such as the die coating method, the roll coating method, the ink jet method, or the spray coating method, is preferable from viewpoints of easily obtaining a homogeneous thin film and high productivity.

In the wet method, examples of a liquid medium in which the light emitting layer material is dissolved or dispersed include: a ketone such as methyl ethyl ketone or cyclohexanone; a fatty acid ester such as ethyl acetate; a halogenated hydrocarbon such as dichlorobenzene; an aromatic hydrocarbon such as toluene, xylene, mesitylene, or cyclohexylbenzene; an aliphatic hydrocarbon such as cyclohexane, decalin, or dodecane; and an organic solvent such as dimethylformamide (DMF) or dimethylsulfoxide (DMSO).

In a case where the light emitting layer material is dispersed in a liquid medium, the light emitting layer material can be dispersed by a dispersing method such as an ultrasonic wave, high shear force dispersion, or media dispersion.

In a case where the vapor deposition method is adopted as the method for forming the light emitting layer, vapor deposition conditions therefor depend on the kind of a compound to be used or the like. However, in general, the conditions are desirably selected appropriately from ranges that a boat heating temperature is 50 to 450° C., the degree of vacuum is $10^{-6}$ to $10^{-2}$ Pa, a vapor deposition speed is 0.01 to 50 nm/sec, a substrate temperature is −50 to 300° C., and a layer thickness is 0.1 nm to 5 µm, preferably 5 to 200 nm.

[1. Light Emitting Dopant]

As the light emitting dopant, a fluorescent dopant (also referred to as a fluorescence dopant or a fluorescent compound) or a phosphorescent dopant (also referred to as a phosphorescence dopant or a phosphorescent compound) is preferably used. The concentration of the light emitting dopant in the light emitting layer can be arbitrarily determined based on requirements of a specific dopant and a device used. The concentration of the light emitting dopant may be a uniform concentration with respect to a layer thickness direction of the light emitting layer or may have any concentration distribution.

The light emitting layer may contain a plurality of kinds of light emitting dopants. For example, a combination of dopants having different structures or a combination of a fluorescent dopant and a phosphorescent dopant may be used. This makes it possible to obtain any light emission color.

In the organic EL element, preferably, one or a plurality of light emitting layers contains a plurality of light emitting dopants having different light emission colors, and exhibits white light emission as the entire organic EL element. The combination of light emitting dopants exhibiting white is not particularly limited, but examples thereof include a combination of blue and orange and a combination of blue, green, and red. When front luminance at a viewing angle of 2° is measured with a spectral radiance meter, the white in the organic EL element preferably has chromaticity in a CIE 1931 color system at 1000 cd/m² within a region satisfying x=0.39±0.09 and y=0.38±0.08.

[1-1. Phosphorescent Dopant]

The phosphorescent dopant is a compound in which light emission from an excited triplet is observed, and is specifically a compound that emits phosphorescence at room temperature (25° C.) and has a phosphorescence quantum yield of 0.01 or more at 25° C. The phosphorescent dopant used for the light emitting layer preferably has a phosphorescence quantum yield of 0.1 or more.

The phosphorescence quantum yield can be measured by a method described in Spectroscopy II of the fourth edition of Experimental Chemistry Course 7, p. 398 (1992 edition, Maruzen). The phosphorescence quantum yield in a solution can be measured using various solvents. The phosphorescent dopant used for the light emitting layer only needs to satisfy the above phosphorescence quantum yield (0.01 or more) in any solvent.

The phosphorescent dopant can be appropriately selected from known materials used for the light emitting layer of the organic EL element and used.

Among the materials, preferable examples of the phosphorescent dopant include an organometallic complex having Ir as a central metal. A complex containing at least one coordination mode of a metal-carbon bond, a metal-nitrogen bond, a metal-oxygen bond, and a metal-sulfur bond is more preferable.

[1-2. Fluorescent Dopant]

The fluorescent dopant is a compound capable of emitting light from an excited singlet, and is not particularly limited as long as light emission from an excited singlet is observed.

Examples of the fluorescent dopant include an anthracene derivative, a pyrene derivative, a chrysene derivative, a fluoranthene derivative, a perylene derivative, a fluorene derivative, an arylacetylene derivative, a styrylarylene derivative, a styrylamine derivative, an arylamine derivative, a boron complex, a coumarin derivative, a pyran derivative, a cyanine derivative, a croconium derivative, a squarylium derivative, an oxobenzanthracene derivative, a fluorescein derivative, a rhodamine derivative, a pyrylium derivative, a perylene derivative, a polythiophene derivative, and a rare earth complex-based compound.

A light emitting dopant or the like utilizing delayed fluorescence may also be used as the fluorescent dopant.

Specific examples of the light emitting dopant utilizing delayed fluorescence include compounds described in WO 2011/156793 A, JP 2011-213643 A, and JP 2010-93181 A.

[2. Host Compound]

The host compound is mainly responsible for injecting and transporting charges in the light emitting layer, and its own light emission is not substantially observed in the organic EL element.

The host compound preferably has a phosphorescence quantum yield of less than 0.1 in phosphorescence at room temperature (25° C.), more preferably has a phosphorescence quantum yield of less than 0.01. Among the compounds contained in the light emitting layer, a mass ratio of the host compound in the layer is preferably 20% or more.

In addition, excited state energy of the host compound is preferably higher than excited state energy of the light emitting dopant contained in the same layer.

The host compound may be used singly or in combination of a plurality of kinds thereof. By using a plurality of kinds of host compounds, movement of charges can be adjusted, and efficiency of the organic EL element can be enhanced.

As the host compound used for the light emitting layer, a compound conventionally used for the organic EL element can be used. For example, a low molecular compound, a polymer compound having a repeating unit, or a compound having a reactive group such as a vinyl group or an epoxy group may be used.

The known host compound preferably has a high glass transition temperature (Tg) from a viewpoint of preventing an increase in wavelength of light emitted while having hole transporting ability or electron transporting ability, and furthermore from a viewpoint of stability against heat generation during driving of the organic EL element at a high temperature or driving of the element. The host compound preferably has Tg of 80° C. or higher, more preferably has Tg of 100° C. or higher.

Here, the glass transition point (Tg) is a value determined by a method in accordance with JIS-K-7121 using differential scanning colorimetry (DSC).

However, a material of the light emitting dopant and a material of the host compound are selected such that Ip of the host compound of the light emitting layer is deeper than Ip of the dopant of the light emitting layer by 0.3 eV or more as described later.

In the organic EL element of the present invention, Ip of the host compound of the light emitting layer is deeper than Ip of the light emitting dopant of the light emitting layer by 0.3 eV or more.

By making Ip of the host compound of the light emitting layer deeper than Ip of the light emitting dopant of the light emitting layer by 0.3 eV or more, recombination occurs on a side of a hole transport layer. Therefore, an influence of the electron transport material is small. As a result, light emission efficiency is improved, and an element lifetime is prolonged.

If the depth of Ip of the host compound of the light emitting layer is less than 0.3 eV with respect to the depth of Ip of the light emitting dopant of the light emitting layer, an influence of the electron transport material is large, light emission efficiency is low, and an element lifetime is short.

Therefore, Ip of the host compound of the light emitting layer is made deeper than Ip of the light emitting dopant of the light emitting layer by 0.3 eV or more. The difference in depth is preferably 0.5 eV or more, and more preferably 0.7 eV or more from a viewpoint of reducing an influence of the electron transport material.

Note that the upper limit of the difference in depth of Ip is not particularly defined, but is preferably 2.0 eV or less, and more preferably 1.5 eV or less from a viewpoint of easily designing a band gap and electron affinity.

In a case where the light emitting layer contains a plurality of host compounds, Ip of a host compound having the shallowest Ip in the light emitting layer is made deeper than Ip of the light emitting dopant of the light emitting layer by 0.3 eV or more. In a case where the light emitting layer contains a plurality of light emitting dopants, Ip of the host compound of the light emitting layer is made deeper than Ip of a light emitting dopant having the deepest Ip in the light emitting layer by 0.3 eV or more.

In the organic EL element of the present invention, a whole of constituent layers preferably contains a polar fluorinated solvent in an amount of 1000 ppm by mass or less. Within this range, charge transfer between organic EL element materials is not impaired, the organic EL element materials do not become crystal grains by reorientation due to energy generated at the time of driving, such as heat, and transportability is not lowered due to charge trap of a crystal grain boundary. Note that the whole of constituent layers preferably contains the polar fluorinated solvent in an amount of 100 ppm by mass or more.

Note that the whole of constituent layers means the whole of layers (organic layers) formed between the positive electrode and the negative electrode.

The details of the polar fluorinated solvent will be described in a method for manufacturing the organic EL element, described later.

In the organic EL element of the present invention, the content of the polar fluorinated solvent in the whole of constituent layers can be measured as follows.

First, on a 30 mm square glass substrate, a sample is manufactured in which layers from a hole injection layer to an electron transport layer are formed in a similar manner to the organic EL element to be measured. From a flat film portion of this sample, two samples of about 1 cm square are cut out. In one of the samples, a part of all the layers from the hole injection layer to the electron transport layer is stripped off with a clean wiper immersed in toluene to form a step. An Ag thin film is sputtered with SC-701 MkII ECO manufactured by Sanyu Electron Co., Ltd. Thereafter, the step is measured using WYKO manufactured by Veeco Instruments Inc. to determine a film thickness. Furthermore, in the other sample cut out, all the layers from the hole injection layer to the electron transport layer are removed by immersion in toluene, and a film area is determined from a mass ratio between the mass before removal and the mass after removal. The sample the area of which has been determined is measured with a temperature-programmed thermal desorption analyzer manufactured by ESCO, Ltd. A desorbed gas component is quantitatively determined from a mass fragment spectrum corresponding to the polar fluorinated solvent used for forming the layers, and a mass ratio of the polar fluorinated solvent per volume of each organic layer laminate is determined. As described above, the content of the polar fluorinated solvent can be determined.

<<Electron Transport Layer>>

The electron transport layer is formed of a material having a function of transporting electrons. In a broad sense, the electron transport layer includes the electron injection layer. A single electron transport layer or a plurality of electron transport layers can be disposed.

The electron transport layer is preferably formed using a coating solution containing an electron transport material described below. The coating solution preferably contains a polar fluorinated solvent. The solubility in the polar fluorinated solvent is preferably lowered in order of a material of the electron transport layer and a material of the light emitting layer.

Conventionally, the electron transport material used for the electron transport layer (in a case of a plurality of electron transport layers, an electron transport layer adjacent to a side of the negative electrode) only needs to have a function of transferring electrons injected from the negative electrode to the light emitting layer. As the material, any compound can be selected from conventionally known compounds and used. Examples of the compounds include metal complexes such as a fluorene derivative, a carbazole derivative, an azacarbazole derivative, an oxadiazole derivative, a triazole derivative, a silole derivative, a pyridine derivative, a pyrimidine derivative, and an 8-quinolinol derivative.

In addition, metal free or metal phthalocyanine, or a compound obtained by replacing an end thereof with an alkyl group, a sulfonic acid group, or the like can also be preferably used as the electron transport material.

Among these compounds, a carbazole derivative, an azacarbazole derivative, a pyridine derivative, and the like are preferable in the present invention, and the azacarbazole derivative is more preferable.

The electron transport layer can be formed by forming a thin film of the electron transport material by a known method such as a die coating method, a blade coating method, a roll coating method, a spray coating method, a curtain coating method, a spin coating method, a casting method, a printing method including an inkjet method, or an LB method, and can be preferably formed by a wet process using a coating solution containing the electron transport material and a fluorinated alcohol solvent.

The layer thickness of the electron transport layer is not particularly limited, but is usually about 5 nm to 5 µm, and preferably 5 to 200 nm. The electron transport layer may have a single layer structure formed of one or more kinds of the above materials.

In addition to the electron transport material, an electron transport layer having a high n-property, doped with an impurity as a guest material, can also be used. Examples thereof are described in JP H4-297076 A, JP H10-270172 A, JP 2000-196140 A, JP 2001-102175 A, and J. Appl. Phys., 95, 5773 (2004).

The electron transport layer in the present invention preferably contains an alkali metal salt of an organic substance. The kind of the organic substance is not particularly limited, and examples thereof include a formate, an acetate, a propionate, a butyrate, a valerate, a caproate, an enanthate, a caprylate, an oxalate, a malonate, a succinate, a benzoate, a phthalate, an isophthalate, a terephthalate, a salicylate, a pyruvate, a lactate, a malate, an adipate, a mesylate, a tosylate, and a benzenesulfonate. The organic substance is preferably a formate, an acetate, a propionate, a butyrate, a valerate, a caproate, an enanthate, a caprylate, an oxalate, a malonate, a succinate, or a benzoate, and more preferably an alkali metal salt of an aliphatic carboxylic acid, such as a formate, an acetate, a propionate, or a butyrate. The aliphatic carboxylic acid preferably has four or less carbon atoms. The organic substance is most preferably an acetate.

The kind of an alkali metal of an alkali metal salt of the organic substance is not particularly limited, and examples thereof include Na, K, Cs, and Li. The alkali metal is preferably K or Cs, and more preferably Cs. Examples of the alkali metal salt of the organic substance include a combination of the organic substance and an alkali metal. The alkali metal salt is preferably Li formate, K formate, Na formate, Cs formate, Li acetate, K acetate, Na acetate, Cs acetate, Li propionate, Na propionate, K propionate, Cs propionate, Li oxalate, Na oxalate, K oxalate, Cs oxalate, Li malonate, Na malonate, K malonate, Cs malonate, Li succinate, Na succinate, K succinate, Cs succinate, Li benzoate, Na benzoate, K benzoate, or Cs benzoate, more preferably Li acetate, K acetate, Na acetate, or Cs acetate, and most preferably Cs acetate.

The content of these doping materials is preferably 1.5 to 35% by mass, more preferably 3 to 25% by mass, and most preferably 5 to 15% by mass with respect to an electron transport layer to be added.

However, a material of the electron transport layer is selected such that the molecular dipole moment of at least one organic compound contained in the electron transport layer is 6.0 debye or more as described later.

In the organic EL element of the present invention, the molecular dipole moment of at least one organic compound contained in the electron transport layer is 6.0 debye or more.

By setting the molecular dipole moment of the organic compound to 6.0 debye or more, an injection barrier is mitigated by an interfacial electric field, and voltage can be lowered.

Therefore, the molecular dipole moment of the organic compound is set to 6.0 debye or more. The molecular dipole moment is preferably 8.0 debye or more, more preferably 10.0 debye or more, and still more preferably 12.0 debye or more from a viewpoint of further mitigating the injection barrier.

Note that the upper limit of the molecular dipole moment of the organic compound is not particularly defined, but is preferably 16.0 debye or less, and more preferably 14.0 debye or less from viewpoints of crystallization and a residual solvent.

The organic compound can be, for example, a compound represented by the following general formula (1).

[Chemical formula 2]

General formula (1)

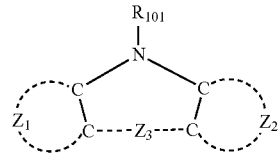

In general formula (1), $Z_1$ and $Z_2$ each independently represent a 6-membered aromatic hydrocarbon ring or a 6-membered aromatic heterocyclic ring which may have a substituent, and $Z_3$ represents a simple bond. In general formula (1), $R_{101}$ represents an aryl group which may have a substituent or an aromatic heterocyclic group which may have a substituent.

Examples of the 6-membered aromatic hydrocarbon ring represented by $Z_1$ and $Z_2$ in the general formula (1) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluorantrene ring, a naphthacene ring, a pentacene ring, a perylene ring, a pentaphene ring, a picene ring, a pyrene ring, a pyranthrene ring, and an anthraanthrene ring. Furthermore, the 6-membered aromatic hydrocarbon ring may have a substituent group A which may be included in the substituent represented by $R_{101}$ described later as a substituent.

In the general formula (1), examples of the 6-membered aromatic heterocyclic ring represented by $Z_1$ and $Z_2$ include a pyridine ring, a pyridazine ring, a pyrimidine ring, a pyrazine ring, a triazine ring, a quinoxaline ring, a carboline ring, and a ring in which a carbon atom of a hydrocarbon ring constituting the carboline ring is further replaced with a nitrogen atom. Furthermore, the 6-membered aromatic heterocyclic ring may have a substituent group A which may be included in the substituent represented by $R_{101}$ described later as a substituent.

In the general formula (1), $Z_1$ preferably represents a pyridine ring which may have a substituent, and $Z_2$ preferably represents a benzene ring which may have a substituent.

Alternatively, in the general formula (1), each of $Z_1$ and $Z_2$ preferably represents a pyridine ring which may have a substituent.

With these configurations, nucleophilicity and an intramolecular dipole can be expressed more strongly due to a high electron density on a nitrogen atom. Therefore, a good electron injecting and transporting material is obtained.

The compound represented by general formula (1) preferably contains only carbon, nitrogen, and hydrogen.

With such a configuration, anisotropy of a molecular arrangement is strong, and a better electron injecting and transporting material is obtained.

Examples of the substituent represented by $R_{101}$ in general formula (1) include an aryl group (for example, a phenyl group or a naphthyl group) and an aromatic heterocyclic group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, or a phthalazinyl group).

These substituents represented by $R_{101}$ may further have the substituent group A described below as a substituent. A plurality of these substituents may be bonded to each other to form a ring.

Examples of the substituent group A include an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, or a pentadecyl group), a cycloalkyl group (for example, a cyclopentyl group or a cyclohexyl group), an alkenyl group (for example, a vinyl group or an allyl group), an alkynyl group (for example, an ethynyl group or a propargyl group), an aryl group (for example, a phenyl group or a naphthyl group), an aromatic heterocyclic group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, or a phthalazinyl group), a heterocyclic group (for example, a pyrrolidyl group, an imidazolidyl group, a morpholyl group, or an oxazozolidyl group), an alkoxyl group (for example, a methoxy group, an ethoxy group, a propyloxy group, a pentyloxy group, a hexyloxy group, an octyloxy group, or a dodecyloxy group), a cycloalkoxyl group (for example, a cyclopentyloxy group or a cyclohexyloxy group), an aryloxy group (for example, a phenoxy group or a naphthyloxy group), an alkylthio group (for example, a methylthio group, an ethylthio group, a propylthio group, a pentylthio group, a hexylthio group, an octylthio group, or a dodecylthio group), a cycloalkylthio group (for example, a cyclopentylthio group or a cyclohexylthio group), an arylthio group (for example, a phenylthio group or a naphthylthio group), an alkoxycarbonyl group (for example, a methyloxycarbonyl group, an ethyloxycarbonyl group, a butyloxycarbonyl group, an octyloxycarbonyl group, or a dodecyloxycarbonyl group), an aryloxycarbonyl group (for example, a phenyloxycarbonyl group or a naphthyloxycarbonyl group), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, or a 2-pyridylaminosulfonyl group), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, or a pyridylcarbonyl group), an acyloxy group (for example, an acetyloxy group, an ethylcarbonyloxy group, a butylcarbonyloxy group, an octylcarbonyloxy group, a dodecylcarbonyloxy group, or a phenylcarbonyloxy group), an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, or a naphthylcarbonylamino group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, or a 2-pyridylaminocarbonyl group), a ureido group (for example, a methylureido group, an ethylureido group, a pentylureido group, a cyclohexylureido group, an octylureido group, a dodecylureido group, a phenylureido group, a naphthylureido group, or a 2-pyridylaminoureido group), a sulfinyl group (for example, a methylsulfinyl group, an ethylsulfinyl group, a butylsulfinyl group, a cyclohexylsulfinyl group, a 2-ethylhexylsulfinyl group, a dodecysulfinyl group, a phenylsulfinyl group, a naphthylsulfinyl group, or a 2-pyridylsulfinyl group), an alkylsulfonyl group (for example, a methylsulfonyl group, an ethylsulfonyl group, a butylsulfonyl group, a cyclohexylsulfonyl group, a 2-ethylhexylsulfonyl group, or a dodecylsulfonyl group), an arylsulfonyl group (for example, a phenylsulfonyl group, a naphthylsulfonyl group, or a 2-pyridylsulfonyl group), an amino group (for example, an amino group, an ethylamino group, a dimethylamino group, a butylamino group, a cyclopentylamino group, a 2-ethylhexylamino group, a dodecylamino group, an anilino group, a naphthylamino group, or a 2-pyridylamino group), a halogen atom (for example, a fluorine atom, a chlorine atom, or a bromine atom), a fluorinated hydrocarbon group (for example, a fluoromethyl group, a trifluoromethyl group, a pentafluoroethyl group, or a pentafluorophenyl group), a cyano group, a nitro group, a hydroxy group, a mercapto group, and a silyl group (for example, a trimethylsilyl group, a triisopropylsilyl group, a triphenylsilyl group, or a phenyldiethylsilyl group).

Preferable substituents are an alkyl group, a cycloalkyl group, a fluorinated hydrocarbon group, an aryl group, and an aromatic heterocyclic group.

The simple bond represented by $Z_3$ is a bond for directly bonding substituents to be linked to each other.

The present invention is characterized in that $Z_1$ in the general formula (1) is a 6-membered ring. This makes it possible to further increase the light emission efficiency. Furthermore, this makes it possible to further prolong the lifetime.

The present invention is characterized in that $Z_2$ in the general formula (1) is a 6-membered ring. This makes it possible to further increase the light emission efficiency. Furthermore, this makes it possible to further prolong the lifetime.

Hereinafter, specific examples of at least one organic compound contained in the electron transport layer used in the present invention will be illustrated, but the organic compound is not limited thereto. Incidentally, in Tables, a value of a molecular dipole moment is obtained by rounding off the second decimal place.

TABLE 1
| Formula number | Structural formula | Molecular dipole moment [Debye] |
|---|---|---|
| ET-1 | 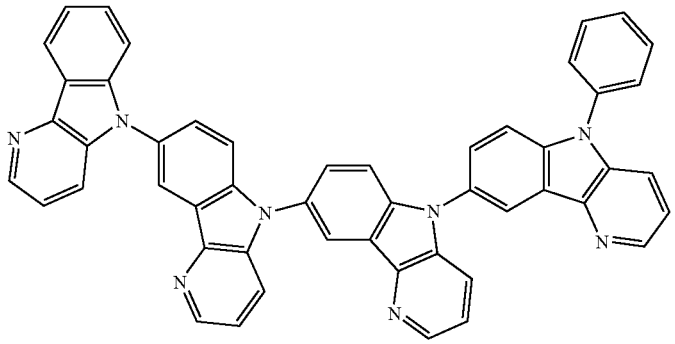 [SMILES: c1ccc(-n2c3ccc(-n4c5ccc(-n6c7ccc(-n8c9ccccc9c9ncccc98)cc7c7ncccc76)cc5c5ncccc54)cc3c3ncccc32)cc1] | 13.8 |
| ET-2 | 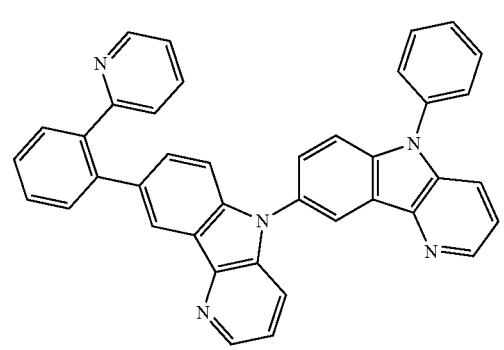 [SMILES: c1ccc(-n2c3ccc(-n4c5ccc(-c6ccccc6-c6ccccn6)cc5c5ncccc54)cc3c3ncccc32)cc1] | 8.6 |
| ET-3 | 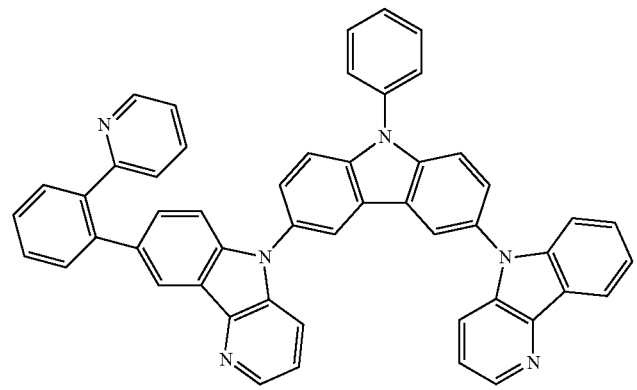 [SMILES: c1ccc(-n2c3ccc(-n4c5ccccc5c5ncccc54)cc3c3cc(-n4c5ccc(-c6ccccc6-c6ccccn6)cc5c5ncccc54)ccc32)cc1] | 7.6 |
| ET-4 | 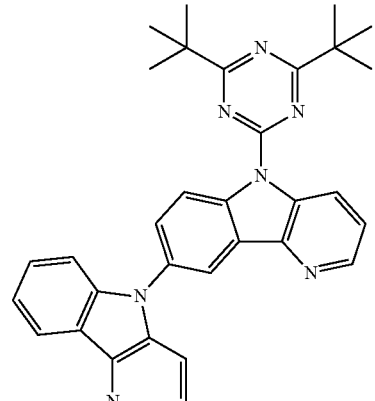 | 6.6 |

TABLE 1-continued

| Formula number | Structural formula | Molecular dipole moment [Debye] |
|---|---|---|
| ET-5 | | 6.6 |

20

TABLE 2

| Formula number | Structural formula | Molecular dipole moment [Debye] |
|---|---|---|
| ET-6 | | 6.2 |
| ET-7 | | 7.6 |

TABLE 2-continued

| Formula number | Structural formula | Molecular dipole moment [Debye] |
|---|---|---|
| ET-8 | | 13.8 |
| ET-9 | | 8.9 |
| ET-10 | | 6.2 |

TABLE 3

| Formula number | Structural formula | Molecular dipole moment [Debye] |
| --- | --- | --- |
| ET-11 | | 6.3 |
| ET-12 | | 6.7 |
| ET-13 | | 11.2 |
| ET-14 | | 10.6 |

TABLE 3-continued

| Formula number | Structural formula | Molecular dipole moment [Debye] |
|---|---|---|
| ET-15 | | 8.4 |

TABLE 4

| Formula number | Structural formula | Molecular dipole moment [Debye] |
|---|---|---|
| ET-16 | | 9.9 |
| ET-17 | | 6.6 |

TABLE 4-continued
| Formula number | Structural formula | Molecular dipole moment [Debye] |
|---|---|---|
| ET-18 | 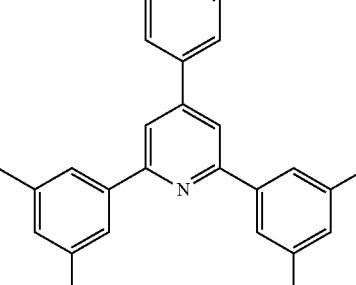 | 7.6 |
| ET-19 | 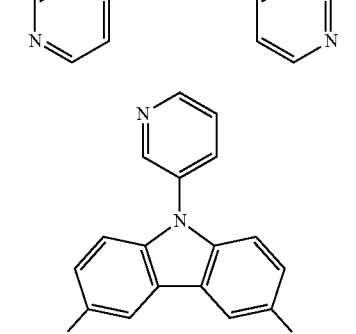 | 7.5 |
| ET-20 | 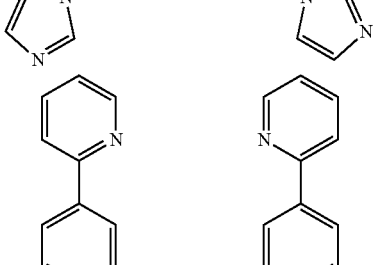 | 6.9 |
TABLE 5
| Formula number | Structural formula | Molecular dipole moment [Debye] |
|---|---|---|
| ET-21 |  | 7.4 |

TABLE 5-continued
| Formula number | Structural formula | Molecular dipole moment [Debye] |
|---|---|---|
| ET-22 | 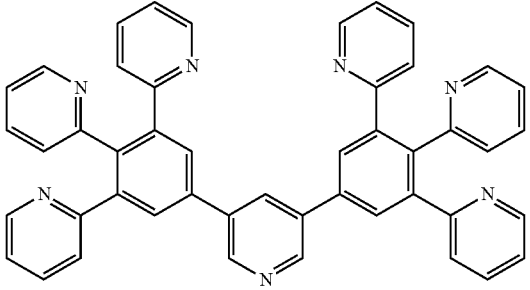 [SMILES: c1ccc(-c2cc(-c3cncc(-c4cc(-c5ccccn5)c(-c5ccccn5)c(-c5ccccn5)c4)c3)cc(-c3ccccn3)c2-c2ccccn2)nc1] | 9.3 |
| ET-23 | 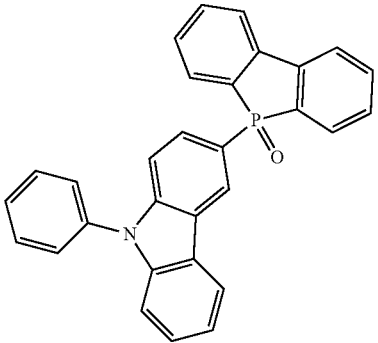 [SMILES: O=P1(c2ccc3c(c2)c2ccccc2n3-c2ccccc2)c2ccccc2-c2ccccc21] | 6.2 |
| ET-24 | 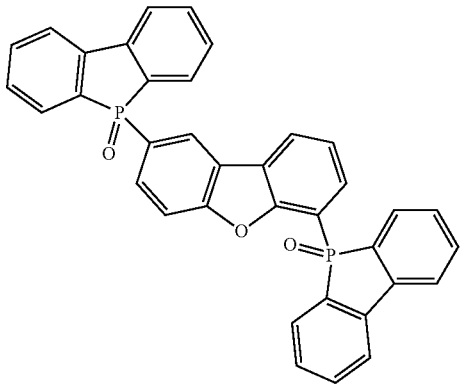 [SMILES: O=P1(c2ccc3oc4c(P5(=O)c6ccccc6-c6ccccc65)cccc4c3c2)c2ccccc2-c2ccccc21] | 7.1 |
| ET-25 | 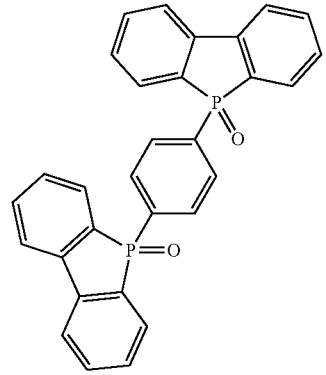 [SMILES: O=P1(c2ccc(P3(=O)c4ccccc4-c4ccccc43)cc2)c2ccccc2-c2ccccc21] | 8.5 |

TABLE 6
| Formula number | Structural formula | Molecular dipole moment [Debye] |
| --- | --- | --- |
| ET-26 | 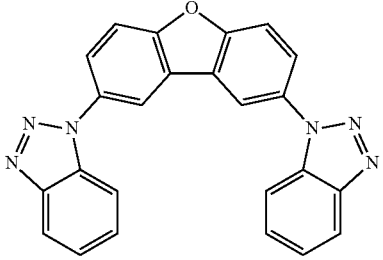 [SMILES: c1ccc2c(c1)nnn2-c1ccc2oc3ccc(-n4nnc5ccccc54)cc3c2c1] | 7.1 |
| ET-27 | 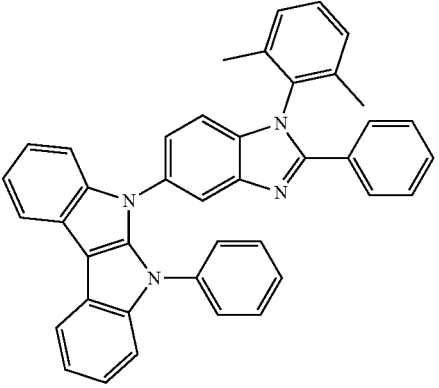 [SMILES: Cc1cccc(C)c1-n1c(-c2ccccc2)nc2cc(-n3c4ccccc4c4c5ccccc5n(-c5ccccc5)c43)ccc21] | 7.8 |
| ET-28 | 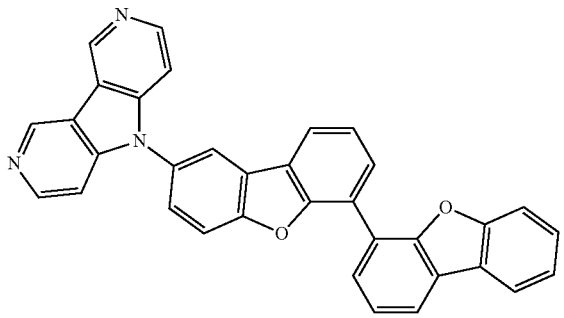 [SMILES: c1ccc2c(c1)oc1c(-c3cccc4c3oc3ccc(-n5c6ccncc6c6cnccc65)cc34)cccc12] | 6.4 |
| ET-29 | 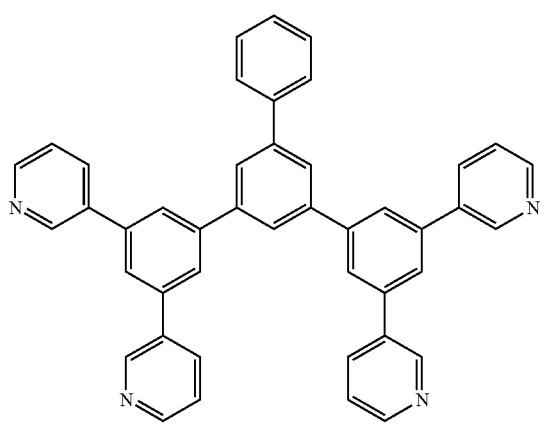 [SMILES: c1ccc(-c2cc(-c3cc(-c4cccnc4)cc(-c4cccnc4)c3)cc(-c3cc(-c4cccnc4)cc(-c4cccnc4)c3)c2)cc1] | 6.4 |

TABLE 6-continued
| Formula number | Structural formula | Molecular dipole moment [Debye] |
|---|---|---|
| ET-30 | 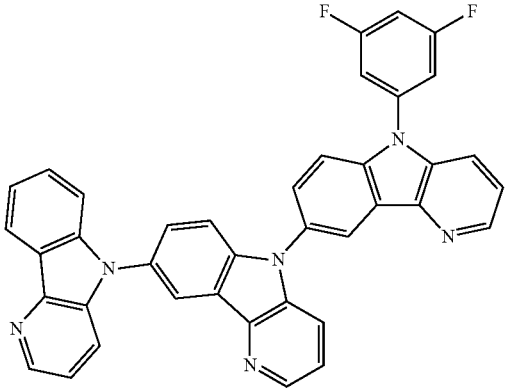 [SMILES: Fc1cc(F)cc(-n2c3ccc(-n4c5ccc(-n6c7ccccc7c7ncccc76)cc5c5ncccc54)cc3c3ncccc32)c1] | 9.7 |
TABLE 7
| Formula number | Structural formula | Molecular dipole moment [Debye] |
|---|---|---|
| ET-31 | 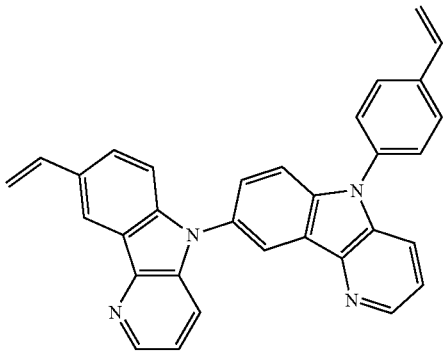 [SMILES: C=Cc1ccc(-n2c3ccc(-n4c5ccc(C=C)cc5c5ncccc54)cc3c3ncccc32)cc1] | 8.0 |
| ET-32 | 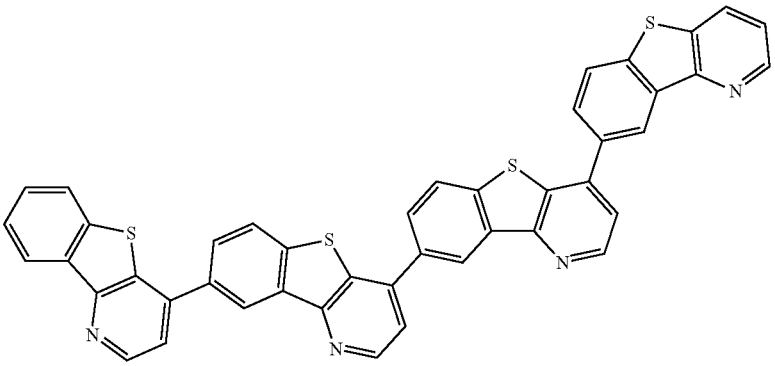 [SMILES: c1ccc2c(c1)sc1c(-c3ccc4sc5c(-c6ccc7sc8c(-c9ccc%10sc%11cccnc%11c%10c9)ccnc8c7c6)ccnc5c4c3)ccnc12] | 7.3 |

TABLE 7-continued
| Formula number | Structural formula | Molecular dipole moment [Debye] |
|---|---|---|
| ET-33 | 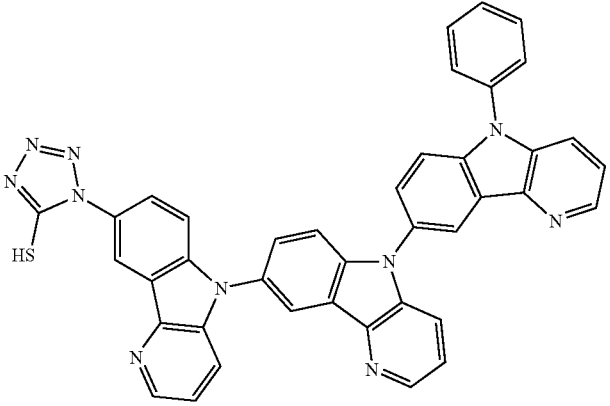 [SMILES: Sc1nnnn1-c1ccc2c(c1)c1ncccc1n2-c1ccc2c(c1)c1ncccc1n2-c1ccc2c(c1)c1ncccc1n2-c1ccccc1] | 16.2 |
| ET-34 | 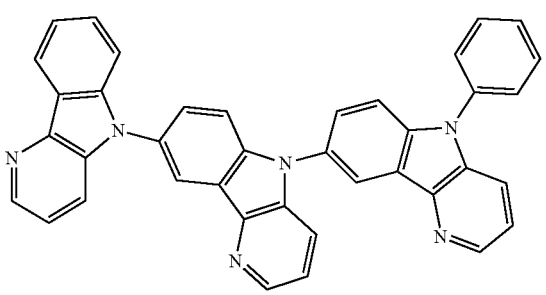 [SMILES: c1ccc(-n2c3ccc(-n4c5ccc(-n6c7ccccc7c7ncccc76)cc5c5ncccc54)cc3c3ncccc32)cc1] | 11.3 |
TABLE 8
| Formula number | Structural formula | Molecular dipole moment [Debye] |
|---|---|---|
| ET-35 | 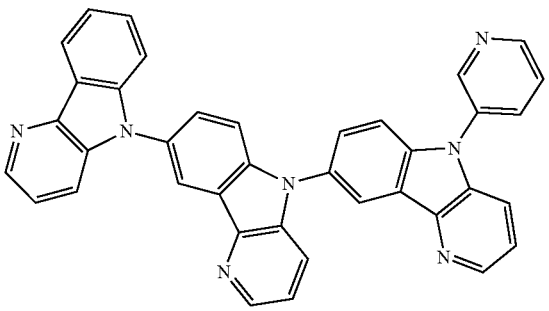 [SMILES: c1cncc(-n2c3ccc(-n4c5ccc(-n6c7ccccc7c7ncccc76)cc5c5ncccc54)cc3c3ncccc32)c1] | 11.4 |
| ET-36 | 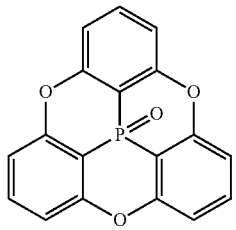 | 6.1 |

<<Hole Transport Layer>>

The hole transport layer is formed of a hole transport material having a function of transporting holes. In a broad sense, the hole injection layer and the electron blocking layer are also included in the hole transport layer. A single hole transport layer or a plurality of hole transport layers can be disposed.

The hole transport material has any one of a hole injection property, a hole transport property, and an electron barrier property, and may be either an organic substance or an inorganic substance. Examples of the hole transport material include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, a conductive polymer oligomer, and a thiophene oligomer.

As the hole transport material, the compounds described above can be used. However, a porphyrin compound, an aromatic tertiary amine compound, and a styrylamine compound can be used, and an aromatic tertiary amine compound is particularly preferably used.

Typical examples of the aromatic tertiary amine compound and the styrylamine compound include N,N,N',N'-tetraphenyl-4,4'-diaminophenyl, N,N'-diphenyl-N,N'-bis(3-methylphenyl)-[1,1'-biphenyl]-4,4'-diamine (abbreviation: TPD), 2,2-bis(4-di-p-tolylaminophenyl) propane, 1,1-bis(4-di-p-tolylaminophenyl) cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl) phenylmethane, bis(4-di-p-tolylaminophenyl) phenylmethane, N,N'-diphenyl-N,N'-di(4-methoxyphenyl)-4,4'-diaminobiphenyl, N,N,N',N'-tetraphenyl-4,4'-diaminodiphenyl ether, 4,4'-bis(diphenylamino) quadriphenyl, N,N,N-tri(p-tolyl) amine, 4-(di-p-tolylamino)-4'-[4-(di-p-tolylamino) styryl] stilbene, 4-N,N-diphenylamino-(2-diphenylvinyl) benzene, 3-methoxy-4'-N,N-diphenylaminostylbenzene, and N-phenylcarbazole. Examples thereof further include a compound having two condensed aromatic rings in a molecule, described in U.S. Pat. No. 5,061,569, such as 4,4'-bis[N-(1-naphthyl)-N-phenylamino] biphenyl (abbreviation: NPD), and 4,4',4"-tris[N-(3-methylphenyl)-N-phenylamino] triphenylamine (abbreviation: MTDATA) in which three triphenylamine units are connected in a star-burst shape, described in JP H4-308688 A.

Furthermore, a polymer material obtained by introducing these materials into a polymer chain, or a polymer material using these materials as a main chain of a polymer can also be used. An inorganic compound such as p-type-Si or p-type-SiC can also be used as a hole injection material and a hole transport material.

A so-called p-type hole transport material as described in JP H11-251067 A and J. Huang et al., Applied Physics Letters, 80 (2002), p. 139 can also be used. The present invention preferably uses these materials from a viewpoint of obtaining a light emitting element having higher efficiency.

The hole transport layer can be formed by forming a thin film of the hole transport material by a known method such as a vacuum vapor deposition method, a die coating method, a blade coating method, a roll coating method, a spray coating method, a curtain coating method, a spin coating method, a casting method, a printing method including an inkjet method, or an LB method The layer thickness of the hole transport layer is not particularly limited, but is usually within a range of about 5 nm to 5 µm, and preferably within a range of 5 to 200 nm. The hole transport layer may have a single layer structure formed of one or more of the above materials.

By doping a material of the hole transport layer with an impurity, a p-property can also be increased. Examples thereof are described in JP H4-297076 A, JP 2000-196140 A, JP 2001-102175 A, and J. Appl. Phys., 95, 5773 (2004).

As described above, a higher p-property of the hole transport layer is preferable because an element with lower power consumption can be manufactured.

<<Injection Layer>>

The injection layer (hole injection layer and electron injection layer) refers to a layer disposed between an electrode and a light emitting layer in order to lower driving voltage or enhance light emission luminance. Details of the injection layer are described in Part 2, Chapter 2, "Electrode Material" (pp. 123 to 166) of "Organic EL element and Frontiers of Industrialization Thereof (issued by NTS Inc. on Nov. 30, 1998). The injection layer includes a hole injection layer and an electron injection layer.

The injection layer can be disposed as necessary. The hole injection layer may be present between an anode and a light emitting layer or a hole transport layer. The electron injection layer may be present between a cathode and the light emitting layer or an electron transport layer.

Details of the hole injection layer are described in JP H9-45479 A, JP H9-260062 A, JP H8-288069 A, and the like. Specific examples thereof include a phthalocyanine layer typified by copper phthalocyanine, an oxide layer typified by vanadium oxide, an amorphous carbon layer, and a polymer layer using a conductive polymer such as polyaniline (emeraldine) or polythiophene.

Details of the electron injection layer are described in JP H6-325871 A, JP H9-17574 A, JP H10-74586 A, and the like. Specific examples thereof include a metal layer typified by strontium or aluminum, an alkali metal halide layer typified by potassium fluoride, an alkaline earth metal compound layer typified by magnesium fluoride, and an oxide layer typified by molybdenum oxide. In the present invention, the electron injection layer is desirably a very thin film, and the layer thickness thereof is preferably within a range of 1 nm to 10 µm although depending on a constituent material.

<<Electron Blocking Layer>>

The electron blocking layer has a function of a hole transport layer in a broad sense. The electron blocking layer is formed of a material having a function of transporting holes and having an extremely small ability to transport electrons, and can improve a probability of recombining electrons and holes by blocking electrons while transporting holes. Furthermore, the configuration of the hole transport layer can be also used as the electron blocking layer as necessary. The layer thickness of the hole blocking layer applied to the present invention is preferably within a range of 3 to 100 nm, and more preferably within a range of 5 to 30 nm.

<<Positive Electrode>>

As the positive electrode in the organic EL element, an electrode material formed of a metal having a large work function (4 eV or more), an alloy, an electrically conductive compound, or a mixture thereof is preferably used. Specific examples of such an electrode material include a conductive transparent material such as a metal including Au, CuI, indium/tin oxide (ITO), $SnO_2$, ZnO, or IZO. In addition, an amorphous material with which a transparent conductive film can be manufactured, such as IDIXO ($In_2O_3$—ZnO), may be used. In the positive electrode, a thin film of these electrode materials may be formed by a method such as vapor deposition or sputtering, and a pattern of a desired shape may be formed by a photolithography method. In a case where pattern precision is not so much required (about 100 μm or more), a pattern may be formed via a mask having a desired shape during vapor deposition or sputtering of the electrode material. In a case where a material that can be applied, such as an organic conductive compound, is used, a wet film forming method such as a printing method or a coating method can also be used. In a case where light emission is extracted from this positive electrode, transmittance is desirably larger than 10%, and sheet resistance as the positive electrode is preferably several hundred Ω/sq. or less. Furthermore, the film thickness is usually selected within a range of 10 to 1000 nm, preferably within a range of 10 to 200 nm although depending on a material <<Negative Electrode>>

Meanwhile, as the negative electrode, an electrode material formed of a metal having a small work function (4 eV or less) (referred to as an electron injecting metal), an alloy, an electrically conductive compound, or a mixture thereof is used. Specific examples of such an electrode material include aluminum, sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Among these materials, a mixture of the electron injecting metal and a second metal having a larger work function value than the electron injecting metal and being stable, for example, a magnesium/silver mixture, a magnesium/aluminum mixture, a magnesium/indium mixture, an aluminum/aluminum oxide ($Al_2O_3$) mixture, a lithium/aluminum mixture, and aluminum are suitable from viewpoints of an electron injection property and durability against oxidation and the like. The negative electrode can be manufactured by forming thin films of these electrode materials by a method such as vapor deposition or sputtering. Sheet resistance as the negative electrode is preferably several hundred Ω/sq. or less, and a film thickness is usually selected within a range of 10 nm to 5 μm, preferably within a range of 50 to 200 nm. Incidentally, in order to transmit light emitted, either one of the positive electrode and the negative electrode in the organic EL element is preferably transparent or semi-transparent because light emission luminance is improved.

By manufacturing a film of the above metal with a film thickness of 1 to 20 nm on the negative electrode and then manufacturing the conductive transparent material mentioned in the description of the positive electrode thereon, the transparent or semi-transparent negative electrode can be manufactured. By applying this, an element in which both the positive electrode and the negative electrode have transparency can be manufactured.

<<Substrate>>

A material of the substrate used for the organic EL element is not particularly limited, and preferable examples thereof include glass, quartz, and a resin film. The material is particularly preferably a resin film capable of imparting flexibility to the organic EL element.

Examples of the resin film include films of a polyester such as polyethylene terephthalate (PET) or polyethylene naphthalate (PEN), polyethylene, polypropylene, a cellulose ester and a derivative thereof such as cellophane, cellulose diacetate, cellulose triacetate (TAC), cellulose acetate butyrate, cellulose acetate propionate (CAP), cellulose acetate phthalate, or cellulose nitrate, polyvinylidene chloride, polyvinyl alcohol, polyethylene vinyl alcohol, syndiotactic polystyrene, polycarbonate, a norbornene resin, polymethylpentene, polyetherketone, polyimide, polyethersulfone (PES), polyphenylene sulfide, a polysulfone, polyether imide, polyether ketone imide, polyamide, a fluorocarbon resin, nylon, polymethyl methacrylate, an acrylic resin, a polyarylate, and a cycloolefin-based resin such as Arton (trade name, manufactured by JSR Corporation) or Apel (trade name, manufactured by Mitsui Chemicals, Inc.).

On a surface of the resin film, a gas barrier film formed of an inorganic or organic coating film, a hybrid coating film formed of both of inorganic and organic coating films, or the like may be formed. The gas barrier film is preferably a gas barrier film having water vapor permeability (25±0.5° C., humidity (90±2)% RH) of 0.01 g/($m^2 \cdot 24$ h) or less measured by a method in accordance with JIS K 7129-1992. Furthermore, the gas barrier film is preferably a high gas barrier film having oxygen permeability of $1 \times 10^{-3}$ mL//($m^2 \cdot 24$ h·atm) or less measured by a method in accordance with JIS K 7126-1987 and water vapor permeability of $1 \times 10^{-5}$ g/($m^2 \cdot 24$ h) or less.

A material for forming the gas barrier film may be any material as long as having a function of suppressing infiltration of moisture, oxygen, or the like. Examples of the material include silicon oxide, silicon dioxide, and silicon nitride. Furthermore, in order to improve brittleness of the gas barrier film, it is more preferable to have a laminated structure of these inorganic layers and a layer formed of an organic material. Laminating order of the inorganic layer and the organic layer is not particularly limited, but the inorganic layer and the organic layer are preferably laminated alternately a plurality of times.

A method for forming the gas barrier film is not particularly limited, and examples thereof include a vacuum vapor deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a laser CVD method, a thermal CVD method, and a coating method. For example, the method is preferably an atmospheric pressure plasma polymerization method as described in JP 2004-68143 A.

<<Sealing>>

Examples of a sealing means used for sealing the organic EL element of the present invention include a method for bonding a sealing member to an electrode and a support substrate with an adhesive.

It is only required to dispose the sealing member so as to cover a display region of the organic EL element, and the sealing member may have a recessed plate shape or a flat plate shape. Transparency and electrical insulation are not particularly limited.

Specific examples of the sealing member include a glass plate/glass film, a polymer plate/polymer film, and a metal plate/metal film. Particular examples of the glass plate/glass film include soda-lime glass, barium/strontium-containing glass, lead glass, aluminosilicate glass, borosilicate glass, barium borosilicate glass, and quartz. Examples of the polymer plate/polymer film include polycarbonate, an acrylic resin, polyethylene terephthalate, polyethylene naphthalate, polyimide, polyethersulfide, and polysulfone. Examples of the metal plate/metal film include a film formed of one or more metals or alloys selected from the group consisting of stainless steel, iron, copper, aluminum, magnesium, nickel, zinc, chromium, titanium, molybdenum, silicon, germanium, and tantalum.

In the present invention, a glass film, a polymer film, and a metal film can be preferably used because a thin film of the organic EL element can be formed. Furthermore, the polymer film preferably has oxygen permeability of $10^{-3}$ g/(m$^2$·24 h) or less and water vapor permeability of $10^{-3}$ g/(m$^2$·24 h) or less. The water vapor permeability and the oxygen permeability are more preferably $10^{-5}$ g/(m$^2$·24 h) or less.

Sandblast processing, chemical etching processing, or the like is used to process the sealing member into a recessed shape. Specific examples of the adhesive include a photocurable or thermosetting adhesive having a reactive vinyl group of an acrylic acid-based oligomer or a methacrylic acid-based oligomer and a moisture curing adhesive such as 2-cyanoacrylate. Examples of the adhesive further include a thermally or chemically curable (two liquid mixing) adhesive such as an epoxy-based adhesive. Examples of the adhesive further include hot melt type polyamide, polyester, and polyolefin. Examples of the adhesive further include a cationically curable and ultraviolet curable epoxy resin adhesive.

A desiccant may be dispersed in the adhesive. The adhesive may be applied to a sealing portion using a commercially available dispenser or by printing such as screen printing.

Outside an electrode facing the support substrate with an organic layer sandwiched therebetween, inorganic and organic layers can be formed so as to cover the electrode and the organic layer in contact with the support substrate to be used as a sealing film. In this case, a material to form the film may be any material as long as having a function of suppressing infiltration of a substance to deteriorate an element, such as moisture or oxygen. Examples of the material include silicon oxide, silicon dioxide, and silicon nitride. Furthermore, in order to improve brittleness of the film, it is preferable to have a laminated structure of these inorganic layers and a layer formed of an organic material. A method for forming these films is not particularly limited, and examples thereof include a vacuum vapor deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a laser CVD method, a thermal CVD method, and a coating method.

An inert gas such as nitrogen or argon, or an inert liquid such as fluorohydrocarbon or silicone oil is preferably injected into a gap between the sealing member and a display region of the organic EL element in a gas phase or a liquid phase. The gap can be put into a vacuum state. A hygroscopic compound can be encapsulated in the gap.

Examples of the hygroscopic compound include a metal oxide (for example, sodium oxide, potassium oxide, calcium oxide, barium oxide, magnesium oxide, or aluminum oxide), a sulfate (for example, sodium sulfate, calcium sulfate, magnesium sulfate, or cobalt sulfate), a metal halide (for example, calcium chloride, magnesium chloride, cesium fluoride, tantalum fluoride, cerium bromide, magnesium bromide, barium iodide, or magnesium iodide), and a perchloric acid (for example, barium perchlorate or magnesium perchlorate). An anhydrous salt is preferably used in the sulfate, the metal halide, and the perchloric acid.

<<Protective Film and Protective Plate>>

A protective film or a protective plate may be disposed outside a sealing film or a film for sealing on a side facing the support substrate with the organic layer sandwiched therebetween in order to increase mechanical strength of the element. In particular, in a case where sealing is performed by the sealing film, the mechanical strength thereof is not necessarily high. Therefore, such a protective film or protective plate is preferably disposed. As a material which can be used for the protective film or the protective plate, a glass film, a polymer film, a metal film, or the like similar to those used for sealing described above can be used, but a polymer film is preferably used from viewpoints of light weight and a thin thickness.

<<Use>>

Since the organic EL element according to the embodiment described above is a surface light emitting body, the organic EL element can be used as various light emission sources. Examples thereof include a lighting device such as domestic lighting or vehicle interior lighting, a backlight for a watch or a liquid crystal, lighting for signboard advertisement, a light source of a traffic signal, a light source of an optical storage medium, a light source of an electrophotographic copying machine, a light source of an optical communication processing machine, and a light source of an optical sensor, but are not limited thereto. The organic EL element can be particularly effectively used as a backlight of a liquid crystal display device combined with a color filter and a light source for lighting.

<<Method for Manufacturing Organic EL Element>>

An example of a method for manufacturing the organic EL element of the present invention will be described specifically by exemplifying a case of manufacturing the organic EL element 10 illustrated in the FIGURE.

First, the positive electrode 12 is formed on the substrate 11. Next, on the positive electrode 12, the hole injection layer 13 and the hole transport layer 14 are formed in this order. Next, the light emitting layer 15 is formed using a light emitting layer forming coating solution containing a polar fluorinated solvent. Next, on the light emitting layer 15, the electron transport layer is formed using an electron transport layer forming coating solution containing a compound having a structure represented by general formula (1) and a polar fluorinated solvent. Next, on the electron transport layer 16, the electron injection layer 17 and the negative electrode 18 are formed.

Note that a method for forming a layer other than the light emitting layer and the electron transport layer constituting the organic EL element 10 may be any one of a wet method, vapor deposition, sputtering, and the like as described above As for formation of the light emitting layer and the electron transport layer, a method such as vapor deposition or sputtering may be used without being limited to the wet method. However, the wet method is preferably used for any layer constituting the organic EL element 10 from a viewpoint of cost.

Finally, the element in which the negative electrode 18 has been formed is sealed. Known members and methods can be used as a sealing means used for sealing the element.

The organic EL element 10 can be manufactured as described above.

[Polar Fluorinated Solvent]

In the method for manufacturing the organic EL element of the present invention, a polar fluorinated solvent is preferably used for forming the light emitting layer and the electron transport layer.

Here, the polar fluorinated solvent refers to a solvent containing a fluorine atom in a solvent molecule and having a relative dielectric constant of 3 or more and a solubility of 5 g/L or more in water at 25° C.

Note that the solubility refers to an upper limit of the gram number of a solute to be dissolved in 1 L of a solvent at 25° C. at 1 atmosphere.

The boiling point of the polar fluorinated solvent is preferably in a range of 50 to 200° C. By setting the boiling point to 50° C. or higher, occurrence of unevenness due to evaporation heat during drying of a coating film can be suppressed more reliably. By setting the boiling point to 200° C. or lower, a solvent can be quickly dried, and the content of the solvent in a layer to be formed is reduced. Therefore, crystal growth in the layer can be suppressed more reliably, and a way of escape of the solvent is not rough. Therefore, density is improved, and current efficiency can be increased. The boiling point is more preferably in a range of 70 to 150° C.

The moisture in the polar fluorinated solvent acts as a quencher of light emission even if the content thereof is extremely small, and therefore the smaller, the better. The content is preferably 100 ppm or less, and more preferably 20 ppm or less.

An impurity other than moisture in the polar fluorinated solvent similarly acts as a quencher of light emission even if the content thereof is extremely small, or generates bubbles or lowers film quality after drying, and therefore the smaller, the better. The content is preferably 100 ppm or less, and more preferably 20 ppm or less. Examples of the impurity other than moisture include oxygen, an inert gas such as nitrogen, argon, or carbon dioxide, a catalyst used in preparation and purification, and an inorganic compound or a metal brought in from an adsorbent, an instrument, and the like.

As the polar fluorinated solvent, for example, a fluorinated alcohol, a fluorinated acrylate, a fluorinated methacrylate, a fluorinated ester, a fluorinated ether, a fluorinated hydroxyalkylbenzene, and a fluorinated amine are preferable. The fluorinated alcohol, the fluorinated ester, and the fluorinated ether are more preferable. The fluorinated alcohol is still more preferable from viewpoints of solubility and a drying property.

The number of carbon atoms of the fluorinated alcohol is preferably 3 to 5, and the polar fluorinated solvent preferably contains a fluorinated alcohol having 3 to 5 carbon atoms from viewpoints of boiling point and solubility of materials.

A position for replacement with a fluorine atom is, for example, the position of a hydrogen atom in an alcohol. A fluorination ratio may be any ratio as long as the solubility of a layer material is not impaired. Fluorination is desirably performed to such an extent that a lower layer material is not eluted.

Examples of the fluorinated alcohol include 1H,1H-pentafluoropropanol, 6-(perfluoroethyl) hexanol, 1H,1H-heptafluorobutanol, 2-(perfluorobutyl) ethanol (FBEO), 3-(perfluorobutyl) propanol, 6-(perfluorobutyl) hexanol, 2-perfluoropropoxy-2,3,3,3-tetrafluoropropanol, 2-(perfluorohexyl) ethanol, 3-(perfluorohexyl) propanol, 6-(perfluorohexyl) hexanol, 1H,1H-(perfluorohexyl) hexanol, 6-(perfluoro-1-methylethyl) hexanol, 1H,1H,3H-tetrafluoropropanol (TFPO), 1H,1H,5H-octafluoropentanol (OFAO), 1H,1H,7H-dodecafluoroheptanol (DFHO), 2H-hexafluoro-2-propanol, 1H,1H,3H-hexafluorobutanol (HFBO), 2,2,3,3,4,4,5,5-octafluoro-1,6-hexanediol, 2,2-bis (trifluoromethyl) propanol, and 1H,1H-trifluoroethanol (TFEO). TFPO, OFAO, and HFBO are preferable from viewpoints of the above-described boiling point and solubility of a layer material.

Examples of the fluorinated ether include hexafluorodimethyl ether, perfluorodimethoxymethane, perfluorooxetane, perfluoro-1,3-dioxolane, and 1,1,2,2-tetrafluoroethyl-2,2,3,3-tetrafluoropropyl ether.

Examples of the fluorinated ester include methyl perfluorobutyrate, ethyl perfluorobutyrate, methyl perfluoropropionate, methyl difluoroacetate, ethyl difluoroacetate, and methyl-2-trifluoromethyl-3,3,3-trifluoropropionate.

In the light emitting layer forming coating solution, the content of the polar fluorinated solvent is preferably 90 to 99.95% by mass.

In the electron transport layer forming coating solution, the content of a compound having the structure of the present invention represented by general formula (1) is preferably 0.05 to 10% by mass, and the content of the polar fluorinated solvent is preferably 90 to 99.95% by mass.

The polar fluorinated solvent may be a mixed solvent of two or more polar fluorinated solvents or may be a mixed solvent of a polar fluorinated solvent and a solvent other than the polar fluorinated solvent. For example, a mixed solvent of a fluorinated alcohol and an alcohol can be used. In a case where a mixed solvent is used, the content of the polar fluorinated solvent is preferably 50% by mass or more.

As described above, the present invention can provide an organic electroluminescent element having high efficiency, a long lifetime, and bending resistance.

In addition, each constituent layer can be formed by a wet method using a material suitable for a coating type organic EL element having a potential for high productivity. Therefore, manufacturing cost is reduced, and economic efficiency is excellent.

EXAMPLES

Hereinafter, the present invention will be specifically described with reference to Examples, but the present invention is not limited thereto.

Solvents used in the following Examples are illustrated in Table 9.

TABLE 9

| Solvent name | Abbreviation | Solvent category | Boiling point (° C.) |
|---|---|---|---|
| 1H,1H-trifluoroethanol | TFEO | Fluorinated alcohol (carbon number: 2) | 75.0 |
| 1H,1H,3H-tetrafluoropropanol | TFPO | Fluorinated alcohol (carbon number: 3) | 109.0 |
| 2H-hexafluoro-2-propanol, 1H,1H,3H-hexafluorobutanol | HFBO | Fluorinated alcohol (carbon number: 4) | 111.0 |
| 1H,1H,5H-octafluoropentanol | OFAO | Fluorinated alcohol (carbon number: 5) | 140.0 |
| 2-(perfluorobutyl) ethanol | FBEO | Fluorinated alcohol (carbon number: 6) | 143.0 |

TABLE 9-continued

| Solvent name | Abbreviation | Solvent category | Boiling point (° C.) |
|---|---|---|---|
| 1H,1H,7H-dodecafluoroheptanol | DFHO | Fluorinated alcohol (carbon number: 7) | 169.0 |
| 1,1,2,2-tetrafluoroethyl-2,2,3,3-tetrafluoropropyl ether | FEFPE | Fluorinated ether | 92.0 |
| Methyl perfluorobutyrate | MFBA | Fluorinated ester | 80.0 |
| 1H,1H-tridecafluoro heptylamine | TDFHA | Fluorinated amine | 129.0 |
| 1,3-bis(hexafluoro-2-hydroxy-2-propyl) benzene | HFHPB | Fluorinated hydroxyalkylbenzene | 117.0 |
| Isopropanol | IPA | Alcohol | 82.6 |

ET-1 and the like used in the following Examples correspond to ET-1 and the like in Tables 1 to 8 described here. Host compounds (H-1 and the like) and light emitting dopants (Dp-1 and the like) used in the following Examples, and electron transport layer materials (EA-1 and the like) in Comparative Examples used are illustrated below. Incidentally, in Tables, a value of an ionization potential is obtained by rounding off the third decimal place, and a value of a molecular dipole moment is obtained by rounding off the second decimal place.

[Chemical formula 3]

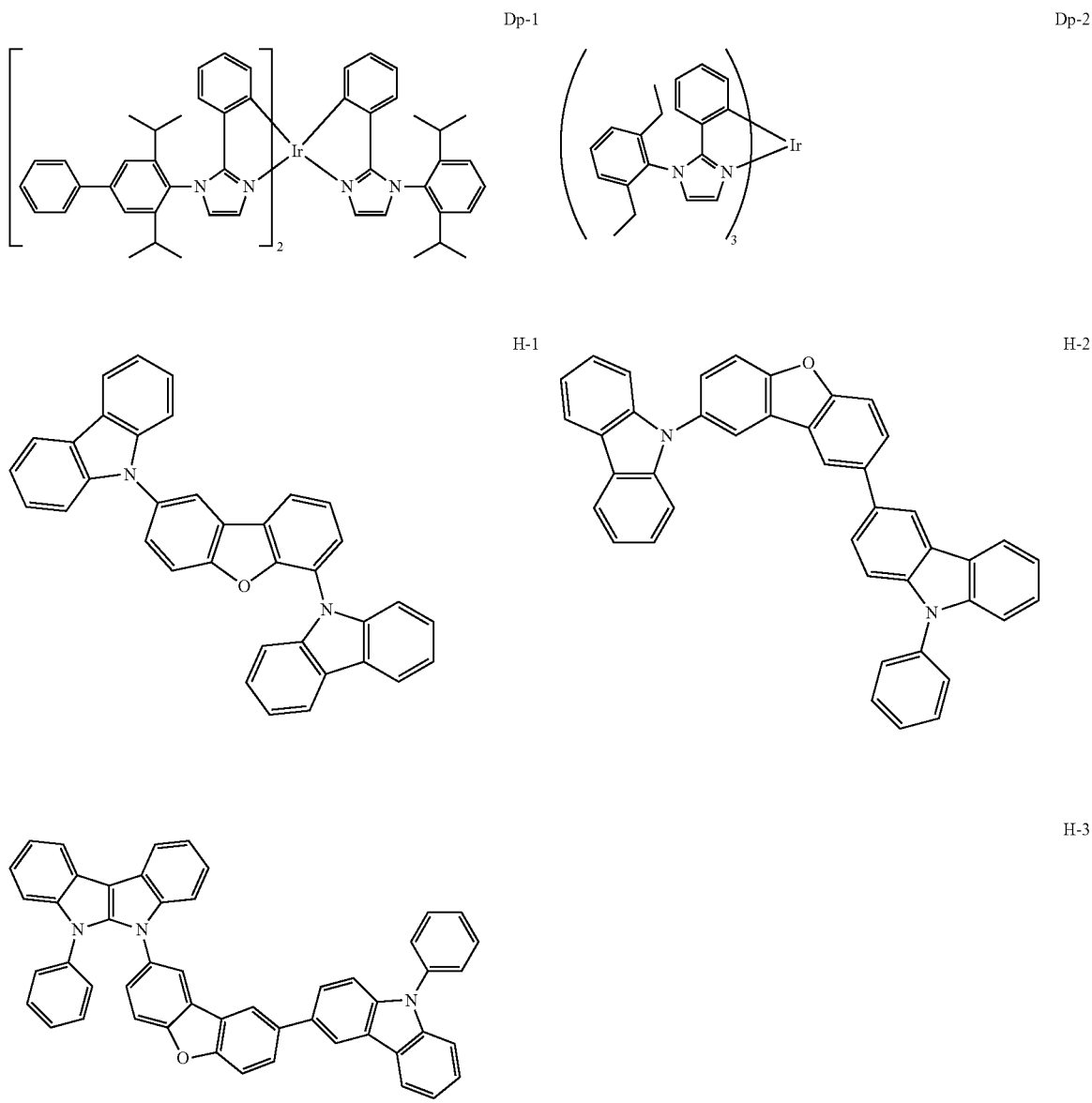

-continued
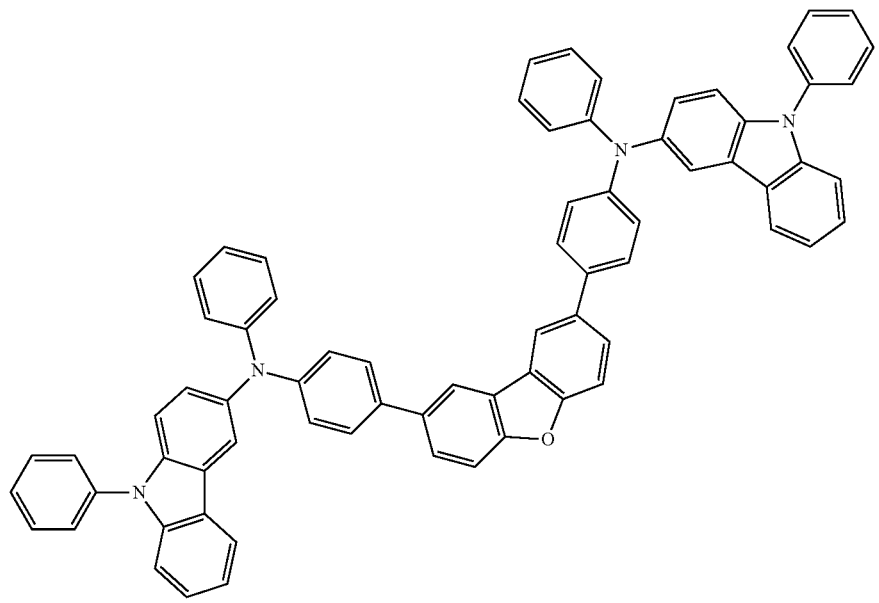
H-4
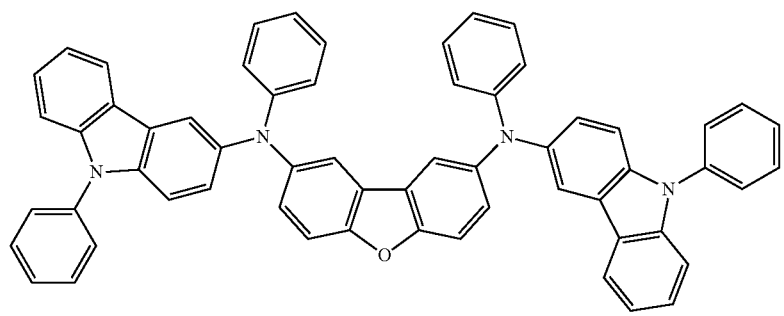
H-5
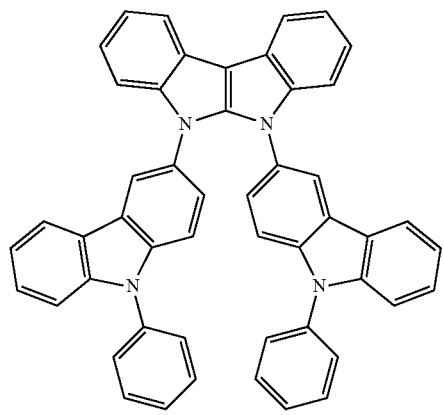
H-6
[Chemical formula 4]
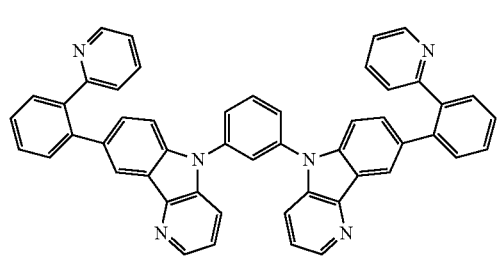
EA-1
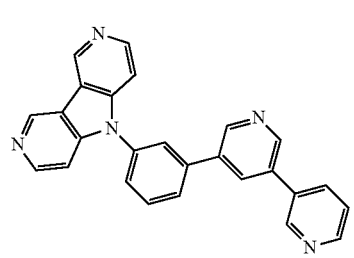
EA-2

-continued

EA-3
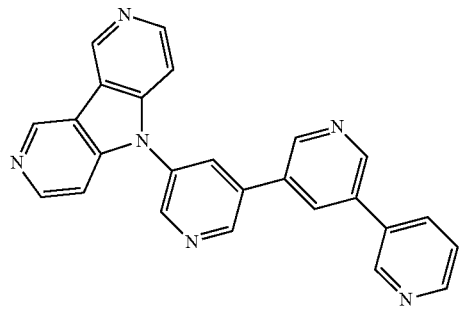

EA-4
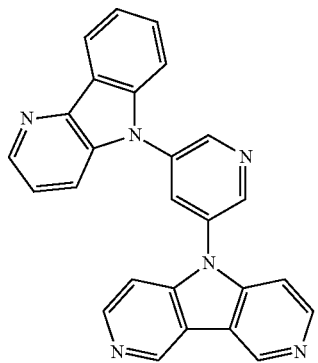

EA-5
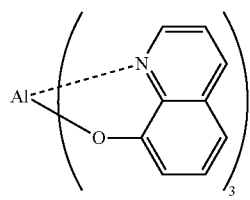

EA-6
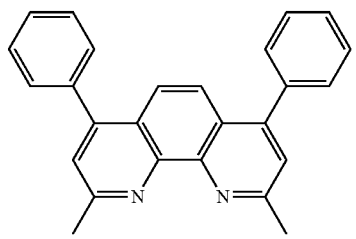

EA-7
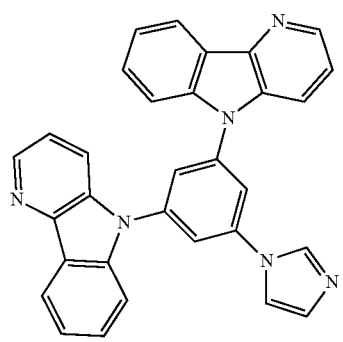

EA-8
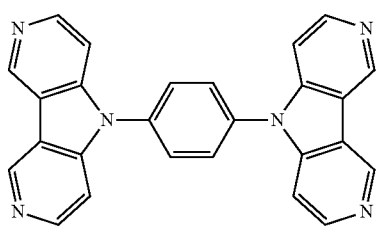

Example 1

<<Manufacture of Organic EL Element 101>>

As described below, positive electrode/hole injection layer/hole transport layer/light emitting layer/electron transport layer/electron injection layer/negative electrode were laminated on a substrate and sealed to manufacture a bottom emission type organic EL element 101.

(Preparation of Substrate)

First, on the entire surface of a polyethylene naphthalate film (manufactured by Teijin DuPont, hereinafter abbreviated as PEN) on a side where a positive electrode is formed, an inorganic gas barrier layer formed of $SiO_x$ was formed so as to have a layer thickness of 500 nm using an atmospheric pressure plasma discharge treatment apparatus having a configuration described in JP 2004-68143 A. As a result, a flexible substrate having a gas barrier property that oxygen permeability was 0.001 mL/(m²·24 h) or less and water vapor permeability was 0.001 g/(m²·24 h) or less was manufactured.

(Formation of Positive Electrode)

A film of indium/tin oxide (ITO) having a thickness of 120 nm was formed on the substrate by a sputtering method and patterned by a photolithography method to form a positive electrode. Note that the pattern was formed such that the area of a light emitting region was 5 cm×5 cm.

(Formation of Hole Injection Layer)

The substrate on which the positive electrode had been formed was ultrasonically cleaned with isopropyl alcohol, dried with dry nitrogen gas, and subjected to UV ozone cleaning for five minutes. Then, to the substrate on which the positive electrode had been formed, a 2% by mass solution obtained by diluting a dispersion of poly(3,4-ethylenedioxythiophene)/Nafion (registered trademark)) prepared in a similar manner to Example 16 of JP 4,509,787 B2 with isopropyl alcohol was applied by a die coating method, and dried naturally to form a hole injection layer having a layer thickness of 40 nm.

(Formation of Hole Transport Layer)

Next, the substrate on which the hole injection layer had been formed was transferred into a nitrogen atmosphere using nitrogen gas (grade Gi). To the substrate, a hole transport layer forming coating solution having the following composition was applied by a die coating method at 5 m/min, dried naturally, and then held at 130° C. for 30 minutes to form a hole transport layer having a layer thickness of 30 nm.

<Hole Transport Layer Forming Coating Solution>

10 parts by mass of hole transport material (following compound (60)) (mass average molecular weight Mw=80000)

3000 parts by mass of chlorobenzene

[Chemical formula 5]

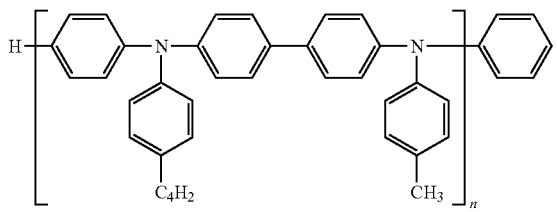

(60)

(Method for Forming Light Emitting Layer)

Next, to the substrate on which the hole transport layer had been formed, a light emitting layer forming coating solution having the following composition was applied by a die coating method at 5 m/min, dried naturally, and then held at 120° C. for 30 minutes to form a light emitting layer having a layer thickness of 50 nm.

<Light Emitting Layer Forming Coating Solution>

9 parts by mass of host compound H-1 (Ip: −5.39 eV)

1 part by mass of phosphorescent dopant Dp-2 (Ip: −4.40 eV)

2,000 parts by mass of isopropyl acetate

Here, a difference in Ip (Alp) between the light emitting dopant and the host compound is −0.99 eV.

(Formation of Electron Transport Layer)

Next, to the substrate on which the light emitting layer had been formed, an electron transport layer forming coating solution having the following composition was applied by a die coating method at 5 m/min, dried naturally, and then held at 80° C. for 30 minutes to form an electron transport layer having a layer thickness of 30 nm.

<Electron Transport Layer Forming Coating Solution>

6 parts by mass of ET-2

2000 parts by mass of 1H,1H,3H-tetrafluoropropanol (TFPO)

(Formation of Electron Injection Layer and Negative Electrode)

Subsequently, the substrate was attached to a vacuum vapor deposition apparatus without exposing the substrate to the atmosphere. Sodium fluoride and potassium fluoride were put in a molybdenum resistance heating boat. The molybdenum resistance heating boat was attached to the vacuum vapor deposition apparatus, and a vacuum chamber was depressurized to $4 \times 10^{-5}$ Pa. Thereafter, the boat was energized and heated, and sodium fluoride was vapor-deposited on the electron transport layer at 0.02 nm/sec to form a thin film having a film thickness of 1 nm. Similarly, potassium fluoride was vapor-deposited on the sodium fluoride thin film at 0.02 nm/sec to form an electron injection layer having a layer thickness of 1.5 nm.

Subsequently, aluminum was vapor-deposited to form a negative electrode having a thickness of 100 nm.

(Sealing)

To the laminate formed through the above steps, a sealing substrate was bonded using a commercially available roll laminating apparatus.

As the sealing substrate, an adhesive layer having a layer thickness of 1.5 μm was disposed on a flexible aluminum foil having a thickness of 30 μm (manufactured by Toyo Aluminum Co., Ltd.) using a two-liquid reaction type urethane-based adhesive for dry lamination, and a polyethylene terephthalate (PET) film having a thickness of 12 μm was laminated thereon.

A thermosetting adhesive as a sealing adhesive was uniformly applied with a thickness of 20 μm along an adhesive surface (gloss surface) of the aluminum foil of the sealing substrate using a dispenser. The resulting product was dried under a vacuum of 100 Pa or less for 12 hours. Furthermore, the sealing substrate was transferred into a nitrogen atmosphere having a dew point temperature of −80° C. or lower and an oxygen concentration of 0.8 ppm and dried for 12 hours or more to perform adjustment such that the moisture content of the sealing adhesive was 100 ppm or less.

As the thermosetting adhesive, an epoxy-based adhesive obtained by mixing the following (A) to (C) was used.

(A) bisphenol A diglycidyl ether (DGEBA)

(B) dicyandiamide (DICY)

(C) epoxy adduct-based curing accelerator

The sealing substrate was disposed in close contact with the laminate and tightly sealed using a pressure bonding roll under pressure bonding conditions that a pressure roll temperature was 100° C., pressure was 0.5 MPa, and an apparatus speed was 0.3 m/min.

As described above, the organic EL element 101 having a similar form to the above-described organic EL element having the configuration illustrated in the FIGURE was manufactured.

<<Manufacture of Organic EL Elements 102 to 144>>

Organic EL elements 102 to 144 were manufactured in a similar manner to manufacture of the organic EL element 101 except that the conditions described in Table 10 were used for forming the electron transport layer.

[Evaluation Method]

(1) Measurement of Light Emission Efficiency

For measurement of light emission efficiency, lighting was performed under a condition of constant current density of 2.5 mA/cm$^2$ at room temperature (25° C.), and the light emission luminance of each element was measured using a spectral radiance meter CS-2000 (manufactured by Konica Minolta Japan, Inc.) to determine light emission efficiency (external extraction efficiency) at the current value. Then, the light emission efficiency of each element was determined as a relative value with the light emission efficiency of the organic EL element 137 (comparison) taken as 100.

(2) Measurement of Light Emission Lifetime

For measurement of a light emission lifetime, an organic EL element was continuously driven under conditions of room temperature of 25° C. and a humidity of 55% RH, luminance was measured using the spectral radiance meter CS-2000, and time (half lifetime) required for the measured luminance to become a half was determined as a scale of a lifetime. As a driving condition, a current value of 10000 cd/m$^2$ at start of continuous driving was used. Then, the light emission lifetime of each element was determined as a relative value with the light emission lifetime of the organic EL element 137 (comparison) taken as 100.

(3) Evaluation of Stability after Storage at High Temperature

Each organic EL element was stored at 85° C. for 24 hours. Thereafter, the light emission luminance of each element in constant current drive at 2.5 mA/cm² was measured before and after storage. A luminance ratio was determined according to the following formula, and used as a scale of storability.

Storability (%)=luminance after storage (2.5 mA/cm²)/luminance before storage (2.5 mA/cm²)×100

(4) Evaluation of Stability after Bending Resistance Test

A bending test of winding each organic EL element onto a roller of 15 mmφ with an Al vapor-deposited PET sealing surface facing upward and then returning the entire resulting product to a flat state was repeated 100 times. After the bending test was performed, the driving voltage of each element in constant current drive at 2.5 mA/cm² was measured. A driving voltage ratio was determined according to the following formula, and used as a scale of bending resistance.

Bending resistance (%)=voltage (2.5 mA/cm²) after bending resistance test/voltage before test (2.5 mA/cm²)×100

(5) Measurement of Content of Polar Fluorinated Solvent

Each layer was formed on a 30 mm square glass substrate in a similar manner to the above organic EL elements. Thereafter, a part of the thin film laminate was stripped off with a clean wiper immersed in toluene. An Ag thin film was sputtered with SC-701 MkII ECO manufactured by Sanyu Electron Co., Ltd. Thereafter, a step at a boundary where the thin film laminate had been stripped off was measured using WYKO manufactured by Veeco Instruments Inc. to determine a film thickness. Furthermore, each thin film laminate was formed on a 30 mm square glass substrate in a similar manner to the above. Thereafter, the wafer was cut into about a 10 mm square, and a film area was determined from a mass ratio between the mass before cut and the mass after cut. The silicon wafer having the area determined above was measured with a temperature-programmed thermal desorption analyzer manufactured by ESCO, Ltd. A desorbed gas component was quantitatively determined from a mass fragment spectrum corresponding to the fluorinated solvent used, and a mass ratio of the fluorinated solvent per volume of each organic layer laminate was determined. Incidentally, in Tables, a case where no dominant peak has not been detected in a mass fragment spectrum corresponding to each fluorinated solvent is represented by "n.d." (not detected).

Table 10 illustrates the results.

TABLE 10

| | Light emitting layer | Electron transport layer | | | Element characteristics | | Evaluation | | | |
|---|---|---|---|---|---|---|---|---|---|---|
| Organic EL element | Film thickness [nm] | Kind of material [formula number] | Molecular dipole moment [Debye] | Solvent used | Light emission efficiency | Light emission lifetime | Stability after storage at high temperature Storability (%) | Stability after bending resistance test Bending resistance (%) | Content of polar fluorinated solvent [ppm by mass] | Note |
| 101 | 60 | ET-2 | 8.6 | TFPO | 135 | 149 | 97 | 102 | 275 | Present invention |
| 102 | 60 | ET-9 | 8.9 | TFPO | 132 | 152 | 96 | 103 | 289 | Present invention |
| 103 | 60 | ET-15 | 8.4 | TFPO | 133 | 137 | 93 | 107 | 302 | Present invention |
| 104 | 60 | ET-13 | 11.3 | TFPO | 134 | 143 | 95 | 104 | 266 | Present invention |
| 105 | 60 | ET-35 | 11.4 | TFPO | 133 | 139 | 97 | 105 | 250 | Present invention |
| 106 | 60 | ET-14 | 10.6 | TFPO | 129 | 137 | 93 | 108 | 278 | Present invention |
| 107 | 60 | ET-3 | 7.6 | TFPO | 133 | 135 | 92 | 105 | 311 | Present invention |
| 108 | 60 | ET-11 | 6.3 | TFPO | 129 | 130 | 90 | 106 | 332 | Present invention |
| 109 | 60 | ET-6 | 6.2 | TFPO | 125 | 127 | 89 | 108 | 345 | Present invention |
| 110 | 60 | ET-1 | 13.8 | TFPO | 132 | 137 | 97 | 104 | 298 | Present invention |
| 111 | 60 | ET-8 | 13.8 | TFPO | 132 | 131 | 95 | 105 | 304 | Present invention |
| 112 | 60 | ET-33 | 16.2 | TFPO | 125 | 122 | 93 | 103 | 322 | Present invention |
| 113 | 60 | ET-16 | 9.9 | TFPO | 129 | 125 | 91 | 109 | 298 | Present invention |
| 114 | 60 | ET-28 | 6.4 | TFPO | 121 | 116 | 82 | 118 | 387 | Present invention |
| 115 | 60 | ET-7 | 7.6 | TFPO | 125 | 126 | 88 | 116 | 335 | Present invention |
| 116 | 80 | ET-2 | 8.6 | TFPO | 134 | 137 | 94 | 104 | 322 | Present invention |
| 117 | 50 | ET-2 | 8.6 | TFPO | 128 | 125 | 90 | 108 | 320 | Present invention |
| 118 | 40 | ET-2 | 8.6 | TFPO | 124 | 114 | 82 | 115 | 314 | Present invention |
| 119 | 60 | ET-8 | 13.8 | HFBO | 132 | 140 | 96 | 107 | 299 | Present invention |
| 120 | 60 | ET-8 | 13.8 | OFAO | 128 | 127 | 91 | 109 | 340 | Present invention |
| 121 | 60 | ET-8 | 13.8 | FBEO | 123 | 128 | 89 | 111 | 363 | Present invention |
| 122 | 60 | ET-8 | 13.8 | FEFPE | 123 | 124 | 93 | 116 | 302 | Present invention |
| 123 | 60 | ET-8 | 13.8 | MFBA | 120 | 121 | 91 | 113 | 287 | Present invention |
| 124 | 60 | ET-8 | 13.8 | TFEO | 115 | 125 | 89 | 116 | 245 | Present invention |
| 125 | 60 | ET-8 | 13.8 | DFHO | 112 | 118 | 81 | 118 | 480 | Present invention |
| 126 | 60 | ET-8 | 13.8 | TDFHA | 110 | 106 | 75 | 123 | 456 | Present invention |
| 127 | 60 | ET-8 | 13.8 | HFHPB | 112 | 108 | 73 | 115 | 390 | Present invention |
| 128 | 60 | ET-8 | 13.8 | IPA | 112 | 114 | 75 | 128 | n.d. | Present invention |
| 129 | 60 | ET-19 | 7.5 | TFPO | 124 | 112 | 81 | 122 | 350 | Present invention |
| 130 | 60 | ET-5 | 6.6 | TFPO | 121 | 118 | 84 | 119 | 365 | Present invention |
| 131 | 60 | ET-22 | 9.3 | TFPO | 125 | 131 | 87 | 115 | 345 | Present invention |
| 132 | 60 | ET-21 | 7.4 | TFPO | 112 | 129 | 85 | 118 | 381 | Present invention |
| 133 | 60 | ET-36 | 6.1 | TFPO | 107 | 108 | 77 | 130 | 412 | Present invention |
| 134 | 60 | ET-24 | 7.1 | TFPO | 110 | 118 | 78 | 129 | 324 | Present invention |
| 135 | 60 | ET-25 | 8.5 | TFPO | 114 | 119 | 81 | 126 | 315 | Present invention |
| 136 | 60 | ET-17 | 6.6 | TFPO | 107 | 112 | 79 | 130 | 354 | Present invention |

TABLE 10-continued

| | | Light emitting layer | Electron transport layer | | | Element characteristics | | Stability after storage at high temperature Storability (%) | Stability after bending resistance test Bending resistance (%) | Content of polar fluorinated solvent [ppm by mass] | Note |
|---|---|---|---|---|---|---|---|---|---|---|---|
| Organic EL element | Film thickness [nm] | | Kind of material [formula number] | Molecular dipole moment [Debye] | Solvent used | Light emission efficiency | Light emission lifetime | | | | |
| 137 | 60 | | ET-2 | 5.6 | TFPO | 100 | 100 | 68 | 138 | 450 | Comparative Example |
| 138 | 60 | | ET-1 | 5.0 | TFPO | 97 | 89 | 60 | 140 | 467 | Comparative Example |
| 139 | 60 | | ET-3 | 4.3 | TFPO | 84 | 85 | 54 | 145 | 490 | Comparative Example |
| 140 | 60 | | ET-4 | 2.2 | TFPO | 79 | 73 | 51 | 145 | 520 | Comparative Example |
| 141 | 60 | | ET-5 | 4.4 | TFPO | 43 | 62 | 48 | 150 | 565 | Comparative Example |
| 142 | 60 | | ET-6 | 2.8 | TFPO | 63 | 56 | 43 | 148 | 538 | Comparative Example |
| 143 | 60 | | ET-7 | 1.2 | TFPO | 60 | 53 | 43 | 150 | 555 | Comparative Example |
| 144 | 60 | | ET-8 | 0.0 | TFPO | 54 | 50 | 40 | 152 | 520 | Comparative Example |

Table 10 indicates that organic EL elements 101 to 136 of the present invention have excellent light emission efficiency, long emission lifetimes, and excellent stability and bending resistance after storage at high temperature as compared with organic EL elements 137 to 144 in Comparative Examples.

Example 2

<<Manufacture of organic EL elements 201 to 206>>

Organic EL elements 201 to 206 were manufactured in a similar manner to manufacture of the organic EL element 101 except that the conditions described in Table 11 were used for forming the light emitting layer and the electron transport layer.

Then, evaluation was performed as in Example 1. Note that the light emission efficiency and the light emission lifetime of each element were determined as relative values with the light emission efficiency and the light emission lifetime of organic EL element 204 (comparison) taken as 100. Table 11 illustrates the results.

TABLE 11

| | Light emitting layer | | | | | Electron transport layer | | |
|---|---|---|---|---|---|---|---|---|
| | Light emitting dopant | | Host compound | | | | | |
| Organic EL element | Kind of material [formula number] | Ip [eV] | Kind of material [formula number] | Ip [eV] | ΔIp [eV] | Kind of material [formula number] | Molecular dipole moment [Debye] | Solvent used |
| 201 | Dp-1 | −4.43 | H-1 | −5.39 | −0.96 | ET-1 | 13.8 | TFPO |
| 202 | Dp-1 | −4.43 | H-2 | −5.27 | −0.84 | ET-1 | 13.8 | TFPO |
| 203 | Dp-1 | −4.43 | H-3 | −4.74 | −0.31 | ET-1 | 13.8 | TFPO |
| 204 | Dp-1 | −4.43 | H-4 | −4.65 | −0.22 | ET-1 | 13.8 | TFPO |
| 205 | Dp-1 | −4.43 | H-5 | −4.60 | −0.17 | ET-1 | 13.8 | TFPO |
| 206 | Dp-1 | −4.43 | H-6 | −4.55 | −0.12 | ET-1 | 13.8 | TFPO |

| | Element characteristics | | Evaluation | | | |
|---|---|---|---|---|---|---|
| Organic EL element | Light emission efficiency | Light emission lifetime | Stability after storage at high temperature Storability (%) | Stability after bending resistance test Bending resistance (%) | Content of polar fluorinated solvent (ppm by mass) | Note |
| 201 | 138 | 142 | 97 | 103 | 292 | Present invention |
| 202 | 136 | 134 | 95 | 104 | 292 | Present invention |
| 203 | 129 | 121 | 92 | 106 | 292 | Present invention |
| 204 | 100 | 100 | 83 | 114 | 292 | Comparative Example |

TABLE 11-continued

| 205 | 89 | 75 | 80 | 120 | 292 | Comparative Example |
| 206 | 81 | 73 | 78 | 127 | 292 | Comparative Example |

Table 11 indicates that organic EL elements 201 to 203 of the present invention have excellent light emission efficiency, long emission lifetimes, and excellent stability and bending resistance after storage at high temperature as compared with organic EL elements 204 to 206 in Comparative Examples.

As described above, the present invention can achieve an object to provide an organic EL element having high efficiency, a long lifetime, and bending resistance. Furthermore, the organic EL element of the present invention suppresses reduction in luminance at the time of storage at high temperature.

REFERENCE SIGNS LIST

11 Organic electroluminescent element
11 Substrate
12 Positive electrode
13 Hole injection layer
14 Hole transport layer
Light emitting layer
16 Electron transport layer
17 Electron injection layer
18 Negative electrode

The invention claimed is:

1. An organic electroluminescent element comprising: a light emitting layer; and an electron transport layer adjacent to the light emitting layer between a positive electrode and a negative electrode, wherein
a host compound of the light emitting layer has an ionization potential deeper than that of a light emitting dopant of the light emitting layer by 0.3 eV or more and 2.0 eV or less, and
at least one organic compound contained in the electron transport layer has a molecular dipole moment of 8.0 debye or more and 16.0 debye or less, General formula (1)

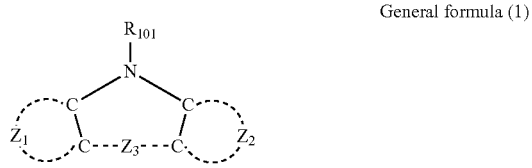

wherein the organic compound is a compound represented by the following general formula (1):
wherein $Z_1$ and $Z_2$ each represent a pyridine ring which may have a substituent, $Z_3$ represents a simple bond, and $R_{101}$ represents an aryl group which may have a substituent or an aromatic heterocyclic group which may have a substituent.

2. The organic electroluminescent element according to claim 1, wherein the molecular dipole moment of the organic compound is 10.0 debye or more and 16.0 debye or less.

3. The organic electroluminescent element according to claim 1, wherein the molecular dipole moment of the organic compound is 12.0 debye or more and 16.0 debye or less.

4. The organic electroluminescent element according to claim 1, wherein the organic compound is a compound represented by general formula (1), containing only carbon, nitrogen, and hydrogen.

5. The organic electroluminescent element according to claim 1, wherein a whole of constituent layers of the organic electroluminescent element contains a polar fluorinated solvent in an amount of 1000 ppm by mass or less.

6. The organic electroluminescent element according to claim 5, wherein the polar fluorinated solvent is any one or more selected from a fluorinated alcohol, a fluorinated ester, and a fluorinated ether.

7. The organic electroluminescent element according to claim 5, wherein the polar fluorinated solvent contains a fluorinated alcohol having 3 to 5 carbon atoms.

8. The organic electroluminescent element according to claim 1, wherein the light emitting layer is formed of a compound having a molecular weight of 500 or more and 3,000 or less.

9. The organic electroluminescent element according to claim 1, wherein the light emitting layer has a film thickness of 50 nm or more and 5 μm or less.

10. The organic electroluminescent element according to claim 2, wherein a whole of constituent layers of the organic electroluminescent element contains a polar fluorinated solvent in an amount of 1000 ppm by mass or less.

11. The organic electroluminescent element according to claim 2, wherein the light emitting layer is formed of a compound having a molecular weight of 500 or more and 3,000 or less.

12. The organic electroluminescent element according to claim 2, wherein the light emitting layer has a film thickness of 50 nm or more and 5 μm or less.

13. The organic electroluminescent element according to claim 3, wherein a whole of constituent layers of the organic electroluminescent element contains a polar fluorinated solvent in an amount of 1000 ppm by mass or less.

14. The organic electroluminescent element according to claim 3, wherein the light emitting layer is formed of a compound having a molecular weight of 500 or more and 3,000 or less.

15. The organic electroluminescent element according to claim 3, wherein the light emitting layer has a film thickness of 50 nm or more and 5 μm or less.

* * * * *